US005997945A

United States Patent [19]

Shasha et al.

[11] Patent Number: 5,997,945
[45] Date of Patent: Dec. 7, 1999

[54] ADHERENT STARCH GRANULES

[75] Inventors: Baruch S. Shasha, Peoria; Michael R. McGuire, Metamora, both of Ill.

[73] Assignee: The United States of America, as represented by the Secretary of Agriculture, Washington, D.C.

[21] Appl. No.: 07/913,565

[22] Filed: Jul. 14, 1992

Related U.S. Application Data

[63] Continuation-in-part of application No. 07/730,763, Jul. 16, 1991, Pat. No. 5,837,273.

[51] Int. Cl.[6] ................................ B01J 13/02; B01J 2/08

[52] U.S. Cl. ....................... 427/213.3; 424/405; 424/407; 424/408; 424/409; 424/410; 424/418; 424/499

[58] Field of Search .................................... 424/405, 406, 424/407, 409, 418, 489, 499; 536/102; 435/178; 127/21; 426/96, 573, 578; 427/213.3

[56] References Cited

U.S. PATENT DOCUMENTS

| | | | |
|---|---|---|---|
| 2,876,160 | 3/1959 | Schoch et al. | 167/32 |
| 3,499,962 | 3/1970 | Wurzburg et al. | 424/489 |
| 3,666,557 | 5/1972 | Jensen et al. | 127/32 |
| 3,672,863 | 6/1972 | Esposito | 71/82 |
| 3,922,354 | 11/1975 | Galluzzi et al. | 426/96 |
| 4,230,687 | 10/1980 | Sair et al. | 424/22 |
| 4,307,115 | 12/1981 | Klopping | 514/477 |
| 4,344,857 | 8/1982 | Shasha et al. | 504/244 |
| 4,382,813 | 5/1983 | Shasha | 504/220 |
| 4,605,622 | 8/1986 | Hasegawa et al. | 435/182 |
| 4,701,326 | 10/1987 | Nelsen et al. | 424/408 |
| 4,755,397 | 7/1988 | Eden et al. | 427/213.3 |
| 4,769,081 | 9/1988 | Maher | 127/33 |
| 4,812,445 | 3/1989 | Eden et al. | 514/60 |
| 4,859,377 | 8/1989 | Shasha et al. | 264/4.1 |
| 4,911,952 | 3/1990 | Doane et al. | 427/213.31 |
| 5,061,697 | 10/1991 | Shasha et al. | 514/60 |
| 5,110,804 | 5/1992 | Lee | 514/60 |
| 5,183,690 | 2/1993 | Carr et al. | 427/213.31 |
| 5,505,940 | 4/1996 | McGuire et al. | 424/93.1 |
| 5,523,083 | 6/1996 | Shasha et al. | 424/93.1 |
| 5,718,969 | 2/1998 | Sewall et al. | 428/304.4 |
| 5,837,273 | 11/1998 | Shasha et al. | 424/405 |

FOREIGN PATENT DOCUMENTS

| | | | |
|---|---|---|---|
| WO85/04074 | 9/1985 | Canada | A01N 25/04 |
| 2014297 | 10/1970 | Germany . | |

OTHER PUBLICATIONS

Koestler, "Microencapsulation by Interfacial Polymerization Techniques—Agricultural Applications," pp. 117–132 In Kydoneius (ed.) Controlled Release Technologies: Methods, Theory, and Applications, CRC Press, Boca Raton (1980).

Lance et al., "Field–Cage and Laboratory Evaluations of Semiochemical–Based Baits for Managing Western Corn Rootworm Beetles (*Coleoptera chrysomelidae*)," J. Econ. Entomol. 83: 1085–1090 (1990).

McGuire et al., "Field Evaluation of Granular Starch Formulations of *Bacillus thuringiensis* Against *Ostrinia nubilalis* (*Lepidoptera: pyrralidae*)," J. Econ. Entomol. 83: 2207–2210 (1990).

McGuire et al., "Evaluation of Starch Encapsulation for Formulation of Grasshopper (*Orthoptera: acrididae*) Entomopoxviruses," J. Econ. Entomol. 84(6): 1652–1656 (1991).

(List continued on next page.)

*Primary Examiner*—Robert H. Harrison
*Attorney, Agent, or Firm*—M. Howard Silverstein; Curtis P. Ribando; John D. Fado

[57] ABSTRACT

The present invention provides methods and compositions used to increase the pest resistance of living organisms. The invention especially provides adherent granules made of starch that are carriers for pest control agents. Simple and economic methods have been developed to prepare said adherent granules. Compositions and characteristics of the granules are disclosed, including their capability for sustained release of pest control agents.

14 Claims, 4 Drawing Sheets

U.S. PATENT DOCUMENTS

Meinke et al., "Pheromone Delivery System: Western Corn Rootworm (*Coleoptera chrysomelidae*) Pheromone Encapsulation in a Starch Borate Matrix," J. Econ. Entomol. 82(6): 1830–1835 (1989).

Metcalf et al., "Cinnamyl Alcohol and Analogs as Attractants for Corn Rootworms (*Coleoptera: chrysomelidae*), " J. Econ. Entomol. 82(6): 1620–1625 (1989).

Raun et al., "Encapsulation as a Technique for Formulating Microbial and Chemical Insecticides," J. Econ. Entomol. 59(3): 620–622 (1966).

Shasha et al., "Starch–Borate Complexes for EPTC Encapsulation," J. Appl. Polym. Sci., 29: 67–73 (1984).

Shotwell, "Evaluation of Baits and Bait Ingredients Used in Grasshopper Control," USDA Tech. Bull. 793 (Mar. 1942).

Synek, "Formulation, Development, and Application of an Insecticide Granule," In Kaneko/Akesson (eds.), Pesticide Formulations and Application Systems; Third Symposium, ASTM STP 828, American Society for Testing and Materials, Philadelphia, pp. 123–131 (1983).

Trimnell et al., "Autoencapsulation: A New Method for Entrapping Pesticides Within Starch," J. Control Release 7: 25–31 (1988).

Trimnell et al., "Entrapment of Herbicides in Starch for Spray Applications," J. Contr. Release 7: 263–268 (1988).

Vander Hooven, "Corncob Granules and Pelleted Carriers—New, Controlled Safer Methods of Handling Pesticides," In Kaneko/Akesson (eds.), Pesticide Formulations and Application Systems: Third Symposium, ASTM STP 828, American Society for Testing and Materials, Philadelphia, pp. 132–140 (1983).

Weissling et al., "Potential of Starch Encapsulated Semiochemical/Insecticide Formulations for Adult Corn Rootworm (*Coleoptera: chrysomelidae*) Control," J. Econ. Entomol. 84: 601–609 (1991).

Wing et al., "Determination of Reaction Variables for the Starch Xanthide Encapsulation of Pesticides," J. Polym. Sci. Polym. Chem. Ed. 21: 121–140 (1983).

Shasha et al., "Slow–Release Formulations of Pesticides," In D. G. Chasin and L. E. Bode (eds.), Pesticide Formulations and Application Systems, American Society for Testing and Materials, Philadelphia, PA.

Trimnell et al., "Pesticide Encapsulation Using a Starch–Borate Complex as Wall Material," J. Appl. Polym. Sci. 27: 3919–3928 (1982).

Dunkle et al., Starch–Encapsulated *Bacillus thuringiensis*: A Potential New Method for Increasing Enviornment Stability of Entomopathogens. Environ. Entomol. 17: 120–126 (1988).

ADHERENT STARCH GRANULES

CROSS-REFERENCE TO RELATED APPLICATION

The present application is a continuation-in-part of U.S. patent application Ser. No. 07/730,763, filed Jul. 16, 1991 U.S. Pat. No. 5,837,273, the disclosure of which is incorporated herein by reference.

TECHNICAL FIELD OF THE INVENTION

The present invention relates to adherent starch-based granules, a process of incorporating a biological or chemical substance such as a pest control agent into such a granule and the use of adherent granules to decrease the population of a pest of a living organism.

BACKGROUND OF THE INVENTION

Myriad approaches have been pursued to control pests. Many of these methods and compositions are directed to control of pests that attack plants, most notably commercially valuable plants. Although much current agricultural research has pest control as its objective, pest destruction of plants and plant products is still a major problem.

Pesticides, biological or chemical agents that kill pests, have been encapsulated in starch which was crosslinked with borate, calcium, or xanthide, thereby producing a matrix that can be processed into granules of desired sizes and densities (Shasha et al., 1984; Trimnell et al., 1982; Wing et al., 1983). However, these methods cannot be used for most living organisms because the reagents and conditions are too harsh for their survival.

Controlled release by means of starch-based encapsulating materials can also be accomplished without the use of chemical crosslinking reactions. In U.S. Pat. No. 2,876,160, Schoch et al. disclose such a method which employs modified, amylose-free starches at concentrations up to 65% solids for embedding water-insoluble materials.

In PCT Int. Appl. WO 85/04074, Flashinski et al. disclose two methods of preparing a starch gel matrix containing an insecticide. The insecticide is either coextruded with a dilute, aqueous dispersion of starch, or the starch is first partially cooked in an extruder prior to cold-blending with the insecticide. In either case, the product is recovered and used as an aqueous gel.

In U.S. Pat. No. 4,230,687, Sair et al. disclose the application of shearing stress, vigorous mechanical working, and heat to distribute an active agent into an enveloping matrix of chemically modified starches, gums, and proteins in the presence of a limited quantity of water. Proteins are used for slow-release matrices; modified starches are used for rapid release.

Similarly, in U.S. Pat. No. 3,922,354, Galuzzi et al. disclose the use of high-shear mixing to incorporate active agents into low-water, high-solid matrices prepared from partially gelatinized unmodified starches. Additives such as modified dextrins, mixtures of mono and diglycerides, toasted cereal solids, and coloring agents are used to control the release of active agents.

In U.S. Pat. No. 3,666,557, Jensen et al. disclose a method of using low-fat starchy materials to microencapsulate individual beadlets of sensitive materials such as vitamins and vegetable oils. Starches are prepared for encapsulation by heating at 88° C. for 30 minutes followed by passage through a homogenizer to effect disruption of granules without degradation of molecules.

One general approach has been to develop carriers for insect control agents. Controlled-release systems based on entrapment of insect control agents in natural polymer matrices have some advantages. For example, hydrated hydrogel capsules have been used to incorporate insecticidally effective amounts of nematodes (U.S. Pat. No. 4,701,326). Capsules in that patent were designed to prevent desiccation. Other types of carriers have been granules.

Insecticides have been formulated on various granule carriers (Synek, 1983; Vander Hooven, 1983). Clay granules have been used to encapsulate entomopathogens (Raun et al., 1966). These carriers may be classified as baits which the insect must feed upon, or inert particles such as clay or corn cob which carry the active agent to the target site and then depend on environmental factors to release the active agent into the feeding zone. Baits have been used in control efforts against grasshoppers (Shotwell, 1944) and, more recently, against European corn borers (McGuire et al., 1990). Because baits must be ingested, they are much more specific than either liquid sprays, dusts, or inert granule carriers.

Integrated pest management programs against ground-dwelling insects such as the fire ant and certain grasshopper species that require selective pesticide usage are areas of application for these types of baits. However, currently available baits have limited utility for controlling most leaf-feeding pests because the granules are easily dislodged from the feeding zone, thus rendering them ineffective against the target pest. Additionally, theoretical calculations show that at application rates of 1 pound/acre, less than 0.01% of the leaf area is covered, assuming particle sizes of approximately 1 millimeter (mm) diameter (Koestler, 1980). To maximize the chances of an insect discovering the granule, volatile attractants may be incorporated into the formulation (e.g. Meinke et al. 1989; Metcalf and Lampmann, 1989; Lance & Sutter 1990).

The granule carriers for insect control agents have generally been suitable only for control of soil-borne pests. They have not been useful for foliar control of insects on plants because they have difficulties sticking to the foliage, or being consequently susceptible to removal by wind, rain, or other disturbing forces. Granule carriers for foliar insect control have neither been efficient nor economic.

Methods for encapsulating entomopathogens within starch matrices have been developed. (Dunkle and Shasha, 1988, and U.S. Pat. No. 4,859,377). Recently, a series of papers has examined the potential for using the Dunkle & Shasha (1988) techniques. One class of agents which were encapsulated within these starch matrices were bacteria, most notably *Bacillus thuringiensis* Berliner for control of European corn borers (McGuire et al., 1990). Grasshopper entomopoxvirus for control of rangeland grasshoppers was similarly formulated (McGuire, et al., 1991).

In another application the starch encapsulation process for preparing a formulation was used to control adult Diabrotica spp. (e.g., Lance and Sutter, 1990; Weissling & Meinke, 1991). Ingredients in the formulation included an attractant, a feeding stimulant (cucurbitacin), and a small amount of insecticide. Although preliminary results were promising, the formulation would not stay in the feeding zone. The development of new, adherent granules is required to aid in this bait approach. A significant problem is that traditional baits generally do not stick well to plant foliage and soon disappear from the feeding zone of the target insect, requiring constant and costly replenishment.

Pesticides were encapsulated by starch xanthate, but methods of production were undesirable due to flammable and toxic components. Other starch-based systems are reviewed by Trimnell and Shasha (1988). These required large numbers of steps placing severe limitations on their commercial use.

A method was developed by Trimnel and Shasha (1988) to form carrier starch granules using relatively small amounts of water. In the Trimnell and Shasha method, a pesticide was mixed with the pregelatinized starch or ungelatinized starch containing a gelatinizing agent and sufficient water to form granules. The sequence of steps in their method was first to mix a solution of chemical herbicide and an organic solvent, and subsequently to add water. By this method granules were formed that encapsulated the pesticide upon contact with the free water. However, these granules required further processing that limited their usefulness.

In addition to deficiencies in the composition of the starch granules, the methods of producing the granules with living entomopathogens, also have serious limitations which become more glaring the more scaled up the production. The basic method (Shasha and Dunkle U.S. Pat. No. 4,859,377) consists of adding water to modified starch at a proportion of at least 1:1 to produce a gelatinous mass. Unfortunately, when the laboratory procedures were scaled up to achieve mass production of the granules, the high water content caused difficulties. Heat could not be applied as a drying agent because entomopathogens will not survive the heat required to effect drying and, thus, would lose their effectiveness. The persistently high water content made grinding and drying of the gelatinous starch mass to produce granules not feasible for most commercial production. Simply reducing the water content resulted in uneven distributions of moisture in the mass.

In summary, despite numerous methods and compositions proposed for pest control, efficacy of granular, pest control agents applied to surfaces, for example, plant foliar surfaces, has not been attained.

BRIEF SUMMARY OF THE INVENTION

The present invention provides, in one aspect, a process of preparing an adherent starch-based granule incorporating a pest control agent, said process comprising the steps of:

(a) admixing, at a temperature of from about 5° C. to about 100° C., an effective incorporating amount of a pregelatinized starch, a pesticidally effective amount of said pest control agent, an effective dispersant amount of a water dispersant and water to form an admixture;

(b) maintaining said admixture under gelation conditions and for a period of time sufficient for said admixture to form an adherent granule; and (c) recovering said granule.

In a preferred embodiment, admixing comprises combining a pesticidally effective amount of the pest control agent, an effective dispersant amount of a water dispersant and water to form a mixture and then mixing the mixture with an effective incorporating amount of pregelatinized starch granules to form an admixture, wherein the pregelatinized starch granules are coated with the pest control agent.

In another preferred embodiment, admixing comprises mixing an effective incorporating amount of a pregelatinized starch, a pesticidally effective amount of the pest control agent and an effective dispersant amount of a water dispersant with water to form an admixture, wherein said pest control agent is encapsulated in said pregelatinized starch.

The pregelatinized starch is preferably corn flour, pearl cornstarch, waxy cornstarch, potato amylopectin or a mixture thereof.

A pest control agent comprises a living pathogen, a chemical pesticide, a pest attractant, a pest phagostimulant or a mixture thereof. A preferred living pathogen is a bacterium such as *B. thuringiensis,* a fungus, a virus, a protozoa or a nematode. A preferred pest attractant is a pheromone or a phagostimulant.

A water dispersant is preferably a water-miscible organic solvent, an inorganic salt, a water absorbent polymer, a sugar, desiccated organismic matter or a mixture thereof. A water-miscible organic solvent is a $C_1$–$C_6$ alcohol, a $C_3$–$C_6$ ketone or a dioxane. More preferably, a water-miscible organic solvent is 2-propanol or acetone.

An inorganic salt is preferably a halide, a sulfate, a phosphate, a carbonate or a mixture thereof. More preferably, an inorganic salt is $CaCl_2$, $(NH_4)_2SO_4$, $Na_2SO_4$, KI, $FeCl_3$ or a mixture thereof.

In a preferred embodiment, the adherent granule adheres to a plant surface and, more preferably a plant foliar surface. In another preferred embodiment, the adherent granule adheres to an external surface of an animal and, preferably skin, fur or hair.

In another aspect, the present invention contemplates a process of decreasing the population of a pest of a living organism comprising delivering to an external surface of said living organism a starch-based granule that (a) incorporates a pest control agent and (b) adheres to that surface. Where the living organism is a plant, the external surface is preferably a foliar surface. Where the living organism is an animal, the external surface is preferably skin, hair or fur. A granule used in that process is preferably prepared in accordance with a process of the present invention.

The present invention, thus, contemplates a process of decreasing the population of a pest of a living organism comprising the steps of:

(a) selecting at least one pest control agent;

(b) incorporating the pest control agent in an adherent granule by (i) admixing, at a temperature of from about 5° C. to about 100° C., a pesticidally effective amount of the pest control agent, an effective incorporating amount of a pregelatinized starch, an effective dispersant amount of a water dispersant and water to form an admixture; (ii) maintaining the admixture under gelation conditions and for a period of time sufficient for the admixture to form a granule that adheres to an external surface of the living organism; and (iii) recovering the granule;

(c) particulating and sieving the granule; and (d) delivering the granule to the external surface of the living organism.

The starch, pest control agent and water dispersant used in a process of decreasing the population of a pest of a living organism are the same as set forth above.

In yet another aspect, the present invention contemplates an adherent starch-based granule that incorporates a pest control agent. Preferably, the starch-based granule is made by a process of the present invention.

The methods and compositions of the present invention solve a significant number of the problems in the previous methods of pest control. A granule of the present invention adheres to an external surface of a living organism despite exposure of those organisms to environmental forces which dislodge other types of granules. Because this invention also provides a new and improved method for preparing such a granule, cost decreases and efficiency increases.

BRIEF DESCRIPTION OF THE DRAWINGS

In the figures which form a portion of the specification:

FIG. 2 shows light stereomicrographs of granules made of Miragel®.

DETAILED DESCRIPTION OF THE INVENTION

Figure 1:
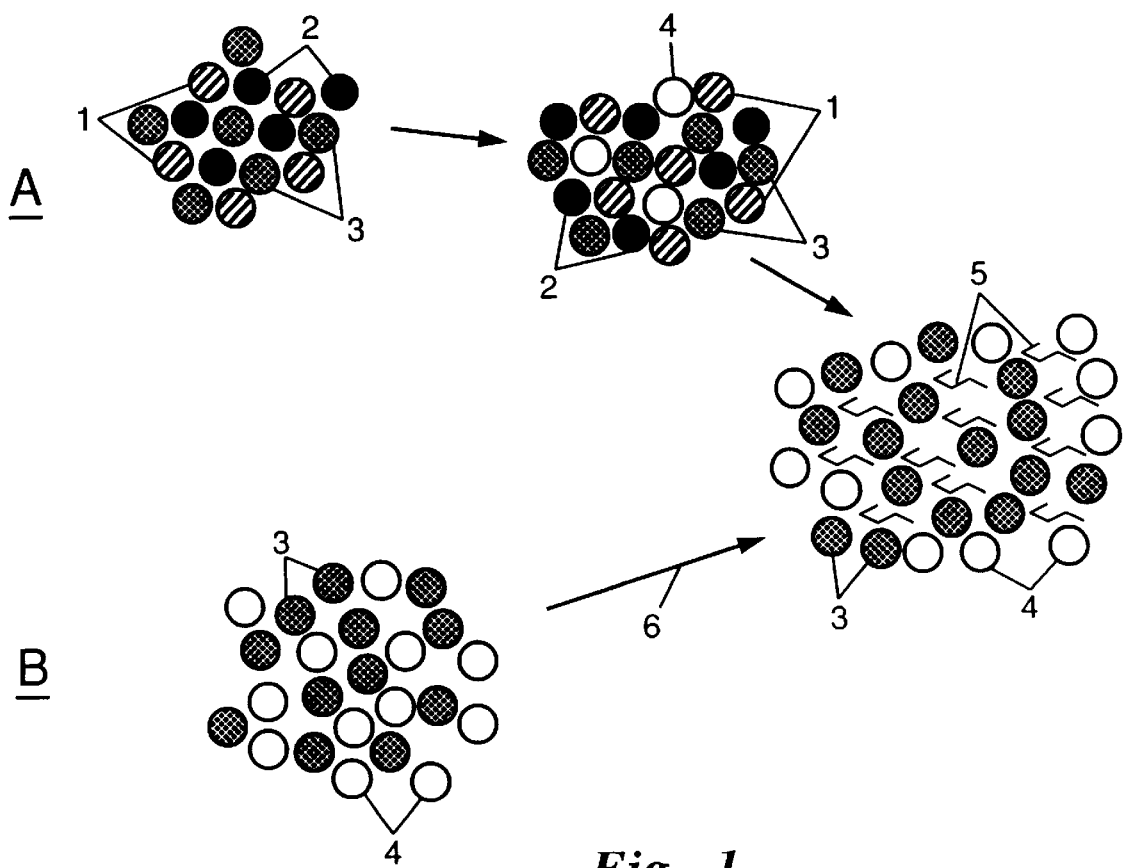
FIG. 1 is a diagrammatic representation of a process of preparing an adherent granule. In panel A, a pest control agent (3) is mixed with a water-miscible organic solvent (1) and water (2). Starch (4) is then admixed with the other ingredients to form granules of gelled starch (5) incorporating the pest control agent (3). In panel B, starch (4) and a pest control agent (3) are admixed with an inorganic salt solution (6) to form granules of gelled starch (5) incorporating the pest control agent (3).

The present invention provides a process of incorporating a chemical or biological material and, in particular a pest control agent in an adherent starch granule and to the composition and structure of such a granule. The present invention also provides a process of decreasing the population of a pest of a living organism. An adherent granule of the present invention comprises starch, a water dispersant and a biological or chemical substance such as a pest control agent.

I. Process of Preparing an Adherent Granule

In one aspect, the present invention provides a process of incorporating a biological or chemical substance and, in particular a pest control agent in an adherent starch granule. Such a process of incorporation comprises the steps of:

(a) admixing, at a temperature of from about 5° C. to about 100° C., an effective incorporating amount of a pregelatinized starch, a pesticidally effective amount of the pest control agent, an effective dispersant amount of a water dispersant and water to form an admixture;

(b) maintaining the admixture under gelation conditions and for a period of time sufficient for the admixture to form an adherent granule; and (c) recovering the granule.

As used herein, the term "adherent" or any of its grammatical equivalents means a granule that sticks to a target surface on which a granule is placed. Exemplary surfaces to which a granule of the present invention adheres include an external surface of a living organism and surfaces made of glass, metal, plastic, wood, and the like. In a preferred embodiment, a granule of the present invention adheres to an external surface of a living organism such as a plant or animal. Where the living organism is a plant, a preferred external surface is a foliar surface. Where the living organism is an animal, a preferred external surface is skin, fur or hair.

As used herein, the phrase "a biological or chemical substance" means any living organism, naturally occuring or synthetic molecule of sufficiently small size to be incorporated by a process of this invention and which substance does not adversely affect any of the ingredients used in accordance with such a process. Typically, a biological or chemical substance is smaller than (has a maximum largest dimension than) about 0.5 millimeters (mm) and, preferably smaller than 0.2 mm. Preferably, a biological or chemical substance is a pest control agent.

As used herein, a "pest control agent" indicates a substance that serves to repel a pest from a living organism, decrease or inhibit the growth, development or destructive activity of a pest. Pests include insects, spiders, fungi, weeds, bacteria and other microorganisms. A pest control agent that can be used in a process of the present invention is a chemical or living pest control agent.

Preferably, a pest control agent comprises a pesticide; an insecticide such as dimilin (N-{[(4-chlorophenyl)amino}carbonyl}-2,6-difluorobenzamide), malathion ((dimethoxyphosphinothioyl)thio]butanedioic acid diethyl ester), carbaryl (1-naphthalenol methylcarbamate) and diazinon (0,0-diethyl O-[6-methyl-2-(1-methylethyl)-4-pyrimidinyl]phosphorothioate); a fungicide; a herbicide such as 2,4-D (2,4-dichlorophenoxyacetate sodium salt), a 2,4-D ester (2,4-dichlorophenoxyacetate isopropyl ester) and metolachlor (2-Chloro-N-(2-ethyl-6-methylphenyl)-N-(2-methoxy-1-benzenedicarboxylate); an antimicrobial; an antibiotic; or an entomopathogen such as a bacterium, a virus, a fungus, a nematode, or a mixture thereof. Pesticides, insecticides, herbicides, fungicides, antimicrobials, antibiotics and entomopathogens are commercially available. An exemplary list of such substances can be found in U.S. Pat. No. 4,911,952, the disclosure of which is incorporated herein by reference.

Exemplary chemical pest control agents include thiocarbonates, dinitroanilines, organophosphates, and alachlor. Exemplary living pest control agents include *B. thuringiensis* and Baculoviridae, e.g., *Autographa californica* nuclear polyhedrosis virus, protozoa such as Nosema spp., fungi such as Beauveria spp., nematodes and a bacteria such as the bacterium *B. thuringiensis*.

As used herein, the phrase "effective amount" means that amount of a pest control agent sufficient to bring about the desired response (e.g., repel or kill a pest). "A pesticidally effective amount" is that amount which, when delivered to an external surface of a living organism, results in a significant mortality rate of a pest when compared to the mortality rate of that same pest exposed to a living organism not treated with that agent.

A pest control agent can further comprise an additive or adjunct such as a dispersant, a phagostimulant (a feeding stimulant), an attractant, an ultraviolet light protectant, a preservative and an inert filler. Examples of such additives can be found in U.S. Pat. No. 4,911,952, the disclosure of which is incorporated herein by reference.

In a preferred embodiment, the additive is an attractant or a phagostimulant. An attractant is preferably an aqueous, non-soluble, or hydrophobic substance that attracts a pest to the granule. A phagostimulant is a substance that stimulates ingestion of the granule.

A preferred attractant is a pheromone or a volatile feeding attractant such as p-methoxycinnamaldehyde. An exemplary and preferred phagostimulant is cucurbitacin obtained from the powdered, dried root of the buffalo gourd, or Coax®, a feeding stimulant containing cotton seed flour, disaccharide, vegetable lipid oil and ethoxylated ester (CCT Corporation, Litchfield Park, Ariz.).

Any pregelatinized starch that forms a gel upon rehydration in an aqueous solvent, and thereafter is amylase digestible can be used in an process of the present invention.

Starch is a readily obtainable natural polymer, composed of amylose and amylopectin, is relatively inexpensive and is capable of forming films. Amylose is essentially a linear polymer having a molecular weight in the range of 100,000–500,000 Daltons. Amylopectin is a highly branched polymer having a molecular weight of up to several million.

When starch is gelatinized in water and cooled, the amylose retrogrades to a much greater extent than the amylopectin fraction.

Retrogradation is a term applied to the phenomenon whereby starch chains in dispersion associate, become insoluble, and precipitate. The rate and extent of retrogradation depends on the properties of the dispersion (pH, temperature, concentration) and on the amount of amylose present in the dispersion. Common cornstarch (pearl) contains about 25% amylose and 75% amylopectin; whereas the waxy corn starches contain only amylopectin. High-amylose starches contain up to 75% amylose.

Preferably, the starch is pearl cornstarch, potato amylopectin, waxy cornstarch, corn flour or a mixture thereof. Pregelatinized starch can be obtained from commercial sources or prepared in accordance with procedures well known in the art.

Miragel®, a pregelatinized cornstarch that passes 100 mesh, is available from Staley Inc., Decatur, Ill. Flour 961 and flour 980 (Illinois Cereal Mills, Paris, Ill.) are partially gelatinized corn flours that pass 60 mesh and +10–20 mesh, respectively. Such partially gelatinized starches as well as pearl cornstarch (CPC International, Englewood Cliffs, N.J.), waxy cornstarch (American Maize Products, Hammond, Ind.), potato amylopectin and "Amylon 5" (National Starch and Chemical Co., New Jersey), and "Staco M" (Staley Co.) can be gelatinized by (1) cooling the starch at a temperature ranging from about 70° C. to about 120° C. and, preferably at about 80° C. for from about 5 seconds to about 30 minutes and, preferably for about 10 minutes and (2) precipitating the cooked starch.

As used herein, the phrase "water dispersant" means an agent that where mixed with a pregelatinized starch and water promotes the uniform and maximum distribution of water throughout the starch so as to promote the uniform and maximum formation of starch granules.

A water dispersant used in accordance with a process of the present invention is a water-miscible organic solvent, an inorganic salt, a water absorbent polymer, a sugar, or desiccated (anhydrous) organismic matter.

Preferably, the water-miscible organic solvent is water soluble. In a preferred embodiment, the water-miscible organic solvent is a $C_1$–$C_6$ alcohol, a $C_3$–$C_6$ ketone, a dioxane or a mixture thereof. Exemplary organic solvents are 2-propanol, methanol, ethanol, n-butanol, acetone and 1,4-dioxane. 2-Propanol is most preferred. Water-miscible organic solvents are commercially available.

An inorganic salt used in accordance with a process of the present invention can be a halide, a sulfate, a phosphate, a carbonate, or a mixture thereof. The cationic component of the salt can be an alkali metal (any member of Group I in the periodic table), an alkaline-earth metal (the heaviest members of Group IIa in the periodic table) or a transition metal selected from the group consisting of elements 21–29, 39–47 and 57–79 in the periodic table. Inorganic salts are commercially available.

Exemplary and preferred salts include calcium chloride ($CaCl_2$), potassium iodide (KI), ammonium sulfate [$(NH_4)_2SO_4$], sodium sulfate ($Na_2SO_4$), sodium carbonate ($Na_2CO_3$) and ferric chloride ($FeCl_3$).

A water absorbent polymer is any hydrophilic or hygroscopic macromolecule that swells in water. Such a polymer can be a synthetic, naturally occurring, organic or inorganic polymer. Exemplary such polymers are gums such as arabic, tragacanth or karaya gum; semisynthetic resins such as carboxymethylcellulose, methylcellulose and modified starches; and synthetic compounds such as ethylene oxides and polyvinyl pyrrolidines. Other water absorbent polymers are well known in the art and commercially available.

As used herein, "desiccated organismic matter" means the solid fraction of matter obtained from a living organism (an animal or plant). Desiccated organismic matter can be obtained by homogenizing organismic matter (living organism) and separating the liquid and solid fractions by desiccation, centrifugation or other suitable means of separation.

A sugar that can be used as a water dispersant is a carbohydrate product of photosynthesis. Exemplary sugars are mono-, oligo- and polysaccharides containing from about 1 to about 50 saccharide units. In a preferred embodiment, a sugar is a disaccharide such as sucrose, or a molasses.

Preferably, a water dispersant is a water-miscible organic solvent, an inorganic salt or desiccated organismic matter.

The use of a water dispersant to produce a granule of the present invention minimizes the water content of formed granules, facilitates aggregation of starch with a pest control agent and enhances adherence of the granule. Upon mixing starch with a water dispersant and water, discrete granules are formed. Although not wishing to be bound by any particular theory, it is believed that when a water dispersant is used, water is not readily accessible to the starch and that competition for the water between the dispersant and the starch delays gelling of the starch (See FIG. 1).

Admixing is carried out at a temperature of from about 5° C. to about 100° C. and, preferably, at a temperature of from about 10° C. to about 25° C. In marked contrast, the encapsulation process of Doane, et al. (U.S. Pat. No. 4,911,952) requires admixing at elevated temperatures in excess of about 120° C.

The starch, pest control agent, water dispersant and water can be admixed in different orders. Where admixing comprises combining a pest control agent, a water dispersant and water to form a mixture and then adding pregelatinized starch granules such as flour 980 to form an admixture, the pregelatinized starch granules are coated with the pest control agent.

Alternatively, where admixing comprises mixing an effective incorporating amount of a pregelatinized starch, a pesticidally effective amount of a pest control agent and an effective dispersant amount of a water dispersant with water to form an admixture, the pest control agent is encapsulated in the pregelatinized starch.

Where the water dispersant is a water-miscible organic solvent, a pregelatinized starch is preferably admixed with a solution of water and the water-miscible organic solvent. The proportions (ratios) of starch, water and water-miscible organic solvent vary inter alia with the nature of the starch and organic solvent. In a preferred embodiment the ratio is about 10:7:3.

Typically, the ratio of water to water-miscible organic solvent is great enough to form granules when mixed with the starch and low enough to prevent formation of a single gelatinous mass. In a preferred embodiment, the ratio of water to water-miscible organic solvent is from about 10:1 to about 10:10 and, more preferably about 10:3.

In accordance with that more preferred embodiment, a 30 percent (v/v) solution of water-miscible organic solvent in water is admixed in about a 1:1 ratio with a pregelatinized starch. The admixing of starch with a solution of water-miscible organic solvent and water has the advantage of minimizing solvent evaporation, thus, reducing the likelihood of forming useless gelatinous blobs and increasing the likelihood of forming adherent granules.

Yet another advantage of admixing starch with a solution of water and a water-miscible organic solvent is formation of an azeotropic mixture. Such an azeotropic mixture facilitates exclusion of water molecules from the starch admixture.

An "effective incorporating amount" of starch, as used herein, means an amount of starch sufficient to incorporate the pest control agent into the starch granule. Typically, the starch is present in an amount such that the concentration of starch in the formed admixture is from about 30 percent by weight to about 70 percent by weight. Preferably, the concentration of starch in the formed admixture is about 50 percent by weight.

The weight percent ratio of starch to water in the admixture is typically from about 10:2 to about 10:13 and, preferably about 10:7.

Where the water dispersant is an inorganic salt, the amount of inorganic salt used depends inter alia on the nature of the starch and inorganic salt selected.

By way of example:
  where the inorganic salt is $CaCl_2$, that ratio is typically from about 4:1 to about 40:1;
  where the inorganic salt is KI, that ratio is typically about 6:1;
  where the inorganic salt is $(NH_4)_2SO_4$, that ratio is typically from about 7:1 to about 13:1;
  where the inorganic salt is $Na_2SO_4$, that ratio is typically about 8:1;
  where the inorganic salt is $Na_2CO_3$, that ratio is typically about 7:1;
  where the inorganic salt is $FeCl_3$, that ratio is typically about 7:1; and
  where the inorganic salt is a mixture of $Na_2SO_4$ and $Na_2CO_3$, that ratio is typically about 9:1.

The inorganic salt is admixed with starch prior to or simultaneously with water. In one embodiment, starch is admixed with a solution comprising an inorganic salt and an aqueous solvent. Where the salt is added as a solution in an aqueous solvent, the concentration of salt in that solution is great enough to avoid the formation of a single gelatinous mass upon initial mixing of salt, starch and water and low enough to avoid saturating the solution with the salt.

In one preferred embodiment, starch is admixed with an inorganic salt solution being from about 30 percent to about 99 percent and, more preferably about 50 percent saturated with that salt. In contrast to the present process, the encapsulation process of Eden et al. (U.S. Pat. No. 4,859,377) contemplates the use of saturated or supersaturated salt solutions.

An aqueous solvent used with an inorganic salt comprises water and, optionally, a water-miscible organic solvent such as disclosed above. A preferred organic solvent as well as a preferred ratio of water and water-miscible organic solvent are the same as set forth above. Where the aqueous solvent comprises a water-miscible organic solvent, the inorganic salt can be admixed with such organic solvent prior to admixing with the starch or the salt and starch can be dry-mixed prior to addition of the organic solvent.

In another embodiment, an inorganic salt is admixed with starch prior to admixture with water or aqueous solvent. In accordance with such an embodiment, the amount of aqueous solvent or water used is dependent upon the nature and formulation of the inorganic salt. The minimum amount of aqueous solvent or water used is that amount needed to permit gelation of substantially all (about 90 percent) the starch and granule formulation.

Where the inorganic salt is an anhydrous hygroscopic salt such as $CaCl_2$, water sufficient for gelation and granule formation is supplied by water in the atmosphere that is adsorbed by the anhydrous salt. In such circumstances, no other water need be added.

By way of example, adherent granules were formed by admixing starch and anhydrous $CaCl_2$ in a weight percent ratio of from about 8:2 to about 39:1, and allowing water to be adsorbed from the air. (See Example 3 hereinafter) If the $CaCl_2$ absorbed a 6-fold molar excess of water [*Hawley's Condensed Chemical Dictionary,* 11th Edition, revised by N. I. Sax and R. J. Lewis, Sr., Van Nostrand Reihold Co., New York (1987], then the admixture of starch, $CaCl_2$ and adsorbed water had a weight percent ratio of starch to water of from about 10:1.6 to about 10:0.2.

One of skill in the art can calculate the amount of anhydrous salts other than $CaCl_2$ needed to form granules with starch.

An admixture formed from starch, a pest control agent, a water dispersant and water is maintained for a period of time and under gelation conditions sufficient for granule formation.

Gelation conditions include temperature, pressure and humidity. Selection of gelation conditions depends predominantly on the nature of the starch, pest control agent, and water dispersant used.

Typically, temperature can range from about 5° C. to about 70° C. and, preferably from about 20° C. to about 30° C. Pressure can range from about 0.5 to about 1.5 atmospheres (atm) and, preferably from about 0.8 to about 1.2 atm. Humidity, expressed as water vapor pressure, at a temperature of about 25° C. and a pressure of about 1.0 atm, is typically from about 20 mmHg to about 60 mmHg and, preferably from about 30 mmHg to about 50 mmHg.

The only limitation for gelation conditions is that those conditions do not adversely affect granule formation, granule structure, granule adherence or pesticidal activity of an incorporated pest control agent. Means for determining gelation conditions for a given granule composition are well known in the art.

Once formed, granules are recovered. Recovering comprises forming discrete, nonagglomerating particles. Where the water dispersant is a water-miscible organic solvent, recovering is evaporating the solvent. Evaporating the water-miscible organic solvent is accomplished by maintaining the formed granules under evaporation conditions for a time period sufficient for removal of that solvent. Evaporation conditions include temperature, pressure and humidity.

The selection of evaporation conditions and time is dependent inter alia on the nature of the solvent and the nature of the encapsulated pest control agent. The only limitation is that the evaporation conditions not adversely affect 1) the structure or adherence of the granules, 2) the pesticidal activity of the encapsulated pest control agent, or 3) granule formation or stability.

Typically, temperature can range from about 20° C. to about 100° C. More preferably, temperature is from about 20° C. to about 30° C. Pressure is typically from about 0.5 atm to about 2.0 atm, and, preferably from about 0.8 atm to about 1.2 atm. The selection of a desired humidity depends upon the selected temperature and pressure. Where the temperature is about 25° C. and the pressure is about 1 atm, humidity (measured as water vapor pressure) is preferably from about 20 mmHg to about 60 mmHg. Means for determining time periods and evaporation conditions for a particular granule composition are well known and readily apparent to a skilled artisan.

Particles can also be prepared by grinding granules using standard procedures well known in the art. Grinding can be performed by hand or using mechanical means such as a blender or a mixture.

Recovering can further comprise sieving the formed particles to obtain particles of a desired size. Sieving is accomplished by passing the particles through meshes or screens of various mesh size. By way of example, particles having a diameter of from about 425 $\mu$m to about 850 $\mu$m pass through 20 mesh but not 40 mesh. (See Example 2, hereinafter.) Typically, the smaller the granule size, the greater the adherence of that granule.

In still another variation of the invention, granular starch-incorporated agents prepared by the aforementioned processes or by other processes as known in the art can be coated with an additional layer of pregelatinized starch. One suitable starch for this purpose is the aforementioned "Miragel®". Another suitable pregelatinized starch that is substantially free of amylose and is commercially sold under the trade name "Mirasperse" (A. E. Staley Co., Decatur, Ill.). The coating is readily accomplished by first wetting the outside of a granule with water, and then contacting the wetted granule with a pregelatinized starch. The advantage of such a coating is that it can serve to tailor the release rate of the active agent. Also, for those types of granules which are not inherently adherent as are those produced in accordance with the aforementioned embodiments of the invention, the added coating tends to make such granules adherent when subsequently contacted with water.

II. Process of Pest Control

In another aspect, the present invention contemplates a process of decreasing the population of a pest of a living organism, which process comprises the steps of:

(a) selecting at least one pest control agent;

(b) incorporating the pest control agent in a starch-based granule in accordance with a process of the present invention;

(c) particulating and sieving the resulting granules; and (d) delivering a pesticidally effective amount of the granules to an external surface of the organism.

Pests are defined herein to include insects, weeds, plant pathogens, and any other agents deleterious to living organisms. A pest control agent that can be used with this process is the same as set forth above in relation to a process of preparing an adherent granule. The selection of a pest control agent depends upon the pest to be controlled as well as the nature of the living organism to be protected. A pesticidally effective amount of a pest control agent incorporated in a granule is delivered to a living organism. Means for determining a pesticidally effective amount for a given pest control agent are well known in the art.

Preferably, the pest control agent comprises at least one of *Bacillus thuringiensis,* entomopoxvirus, a chemical insecticide, and a pest attractant. In a more preferred embodiment, a pest control agent comprises a pesticide and an attractant, the purpose of which is to lure a pest to the granule containing the pest control agent. The attractant can be volatile such as a pheromone.

In a preferred embodiment, granules are delivered as a free-flowing particulate to an external surface of the living organism. Contact of those granules with water, either preexisting on that surface, or subsequently provided, promotes adherence of the granules to that surface. Water can be supplied by rainfall, nocturnal condensation, dew, spraying or irrigation.

Use of an adherent granule of the present invention has the advantage of decreasing the amount of pest control agent needed to protect a given area of surface area by minimizing loss of delivered granules due to environmental conditions. Environmental disturbances include wind, rain and snow.

A major problem in the use of granules prepared by other processes is that such granules are not adherent. In the present invention, a granule is produced which, upon application to a wet surface and being allowed to dry, adheres to that surface even in the presence of additional water.

The use of adherent granules allows for earlier application of a pest control agent and extends the "window" of application necessary for the economic control of a pest that can enter an area over an extended period of time.

III. Adherent Granule

In a still further aspect, the present invention contemplates an adherent starch-based granule that incorporates a biological or chemical substance and, preferably a pest control agent. As used herein, the term "starch-based" indicates that an adherent granule of the present invention comprises starch that serves to incorporate a biological or chemical substance such as a pest control agent. A starch that serves as the basis of an adherent granule is the same as that set forth above in relation to a process of preparing an adherent granule.

An adherent granule of the present invention adheres to a variety of surfaces including but not limited to glass, metal, plastic, wood, plastic and to an external surface of a living organism such as an animal or plant. In a preferred embodiment, an adherent granule of the present invention adheres to an external surface of a plant or animal. Exemplary and preferred surfaces are a plant foliar surface, animal skin, fur and hair. In a preferred embodiment, a starch-based granule of the present invention is made by a process of this invention.

The following examples illustrate particular embodiments of the present invention and are not limiting of the specification and claims in any way.

EXAMPLES

Example 1

Adherence Assays

A. Glass Slide Assay

An incidental aspect of the present invention relates to a process of screening various granule formulations of starch, water, water dispersant and pest control agent for adherence. That screening process has commercial utility because it minimizes the cost of testing various formulations by substituting laboratory tests on glass slides for field tests on an external surface of a living organism. Not only is cost reduced, and space and time saved, but there is absence of risk to the living organisms if the formulations do not work, whereas field tests of ineffective compositions leave these organisms vulnerable to pest attack.

In accordance with a screening process of the present invention, pre-weighed, pre-cleaned glass microscope slides are wetted by spraying the slides with water. About twenty milligrams (mg) of granules are delivered to the wetted slides and the slides are dried (typically at room temperature). The slides having granules thereon are then rinsed with water. Typically, the slides are placed about 2 cm under the delivery tip of a burette. The buret tip is opened and about 40 ml of water are delivered to the slide at a rate of about 20 ml/minute. The slide is moved back and forth under the water stream during the rinse procedure. The rinsed slides are then dried (preferably air dried at room temperature). Those rinsing and drying steps are repeated four times. Following the last drying procedure, the slides are weighed. Granule adherence is calculated as mg of granules remaining on the slide. The data are analyzed for statistical significance using analysis of variance (ANOVA) and least significant differences as appropriate (Lund, 1988).

B. Leaf Assay

An area of about 33 cm² is marked on the surface of each of 20 cotton plant leaves and the marked area is wetted with water. 30 Mg of dry granules are delivered to each of the wetted, marked areas by sprinkling.

Ten leaves are dried immediately. Those dried leaves are removed from the plant and the granules scraped off, dried and weighed.

The remaining 10 leaves are wetted three times over a 7 day period by spraying the marked area with about 5 ml of water at a pressure of about 15 psi. After 7 days, those 10 leaves are dried and the granules scraped off, dried and weighed.

The data are analyzed for statistical significance as set forth above.

Example 2

Studies with Organic Solvent

A. Effects of Solvent Type on Granule Adherence

Granules were produced by admixing about 50 g of Miragel® with 50 milliliters (ml) of an aqueous solvent comprising 35 ml of water and 15 ml of a water-miscible organic solvent. After allowing the gelled mass to granulate, the mass was broken apart in a blender or crumbled to produce granules that passed 20 mesh but not 40 mesh (425 μm to about 850 μm). Formed granules were examined microscopically. The adherence of those granules to glass microscope slides and leaves of cotton plants was determined in accordance with the procedures of Example 1.

1. Microscopic Examination

Figure 3A:
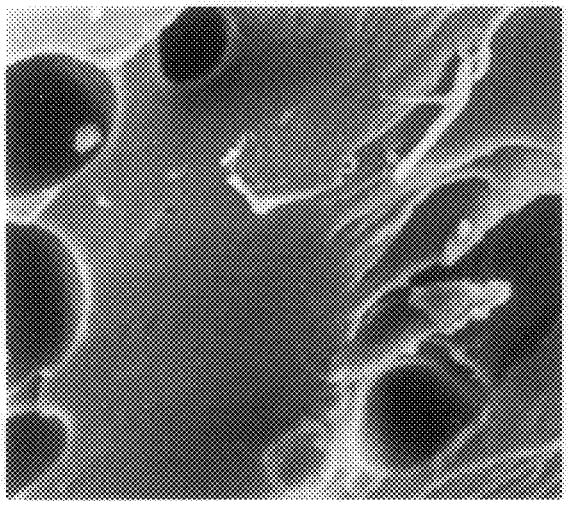
FIG. 3 shows scanning electron micrographs of dry starch granules.
Figure 3B:
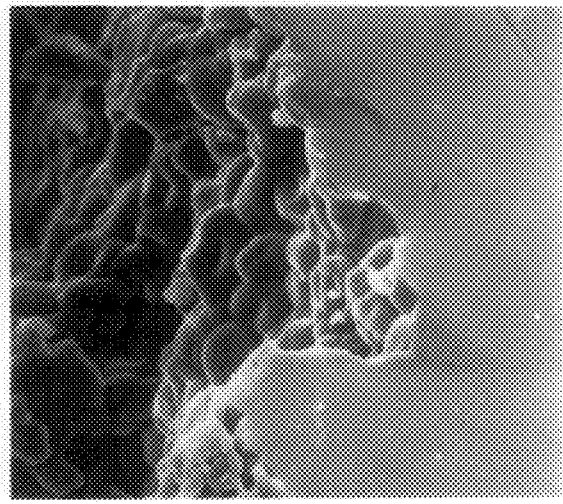
Figure 3C:
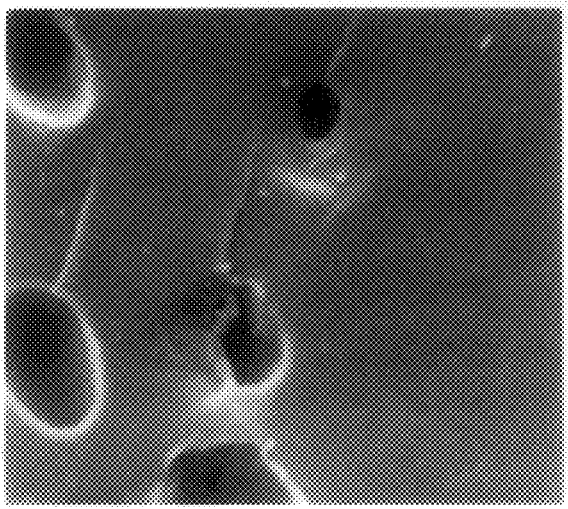
Figure 3D:
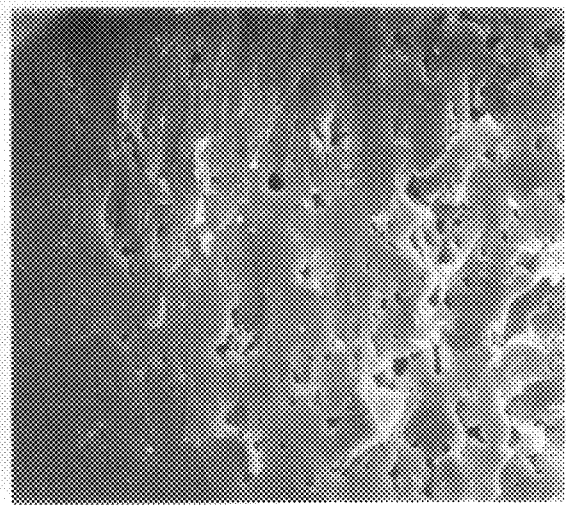

Dried granules made with 2-propanol were more opaque than granules made without 2-propanol (See FIG. 2). In addition, ungelled starch grains were observed on granules made with 2-propanol, whereas no such grains were observed on granules made with water alone (See FIG. 3, panels A and B). Further, smooth surfaces were observed indicating that some of the grains did gel. Numerous small pores were observed inside granules made with 2-propanol but no such pores were observed in granules made with water only (photomicrographs taken at 700x).

Figure 4A:
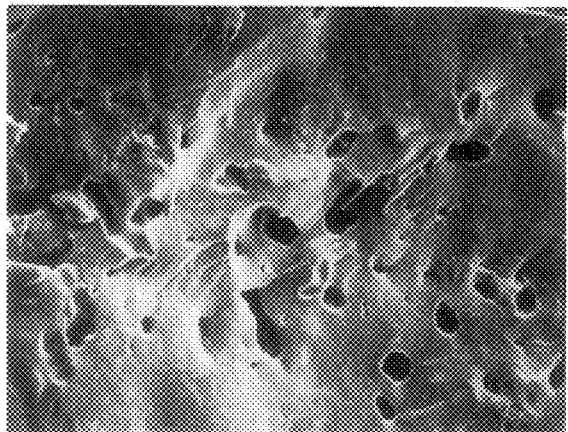
FIG. 4 shows scanning electron micrographs of starch granules after wetting and subsequent drying.
Figure 4B:
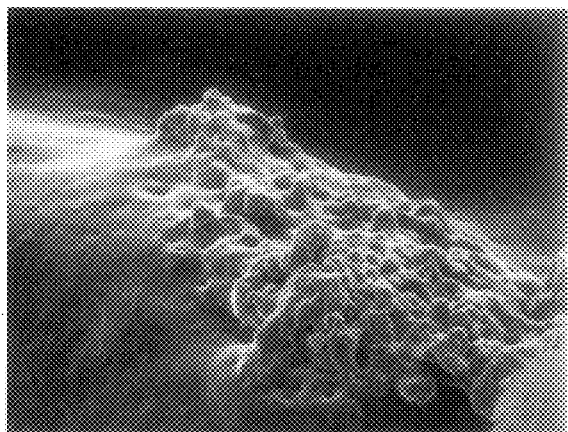
Figure 4C:
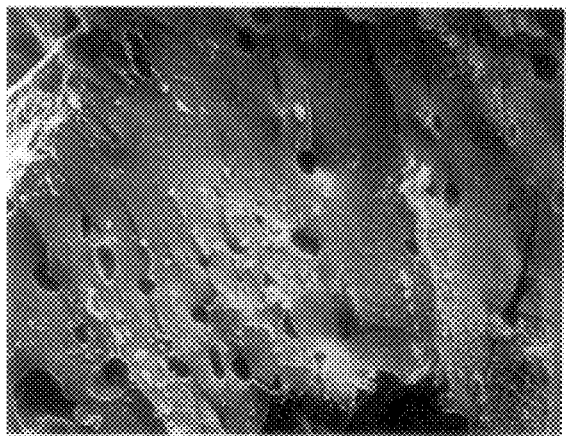
Figure 4D:
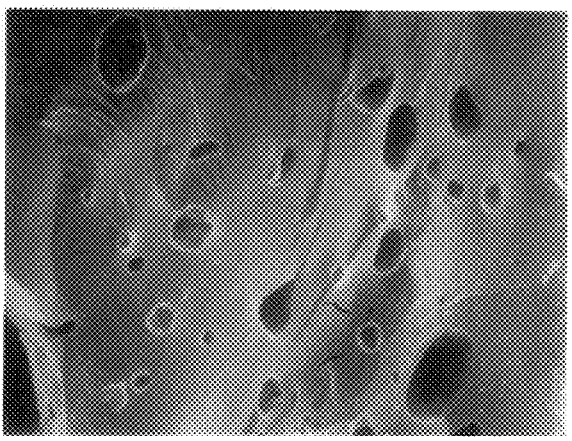
Figure 4A:
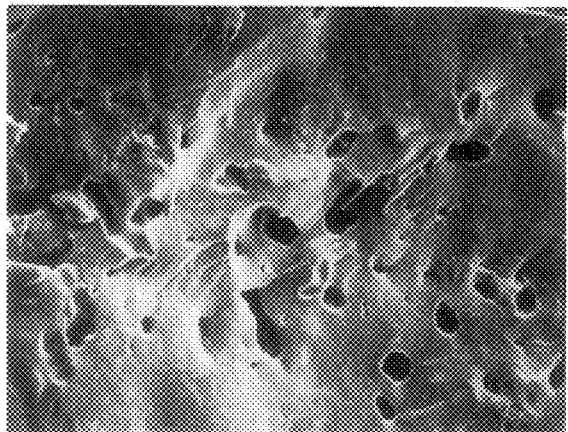
Figure 4B:
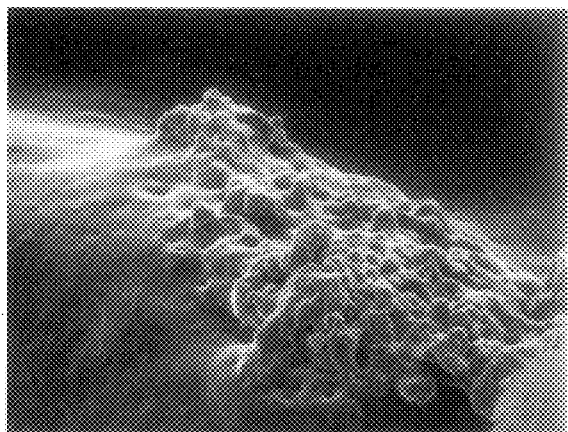
Figure 4C:
Figure 4D:
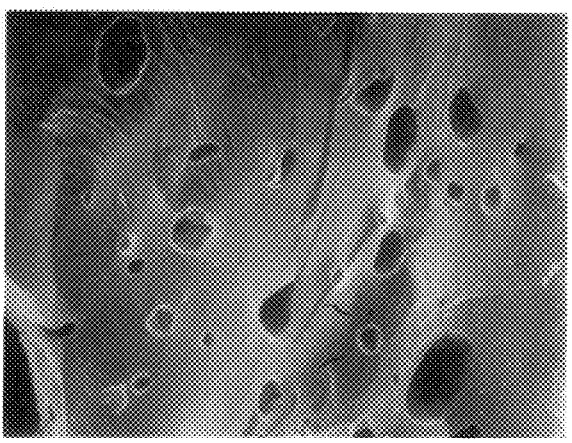

After wetting, both types of granules became transparent and differences between the two types of granules were less apparent. The surface of granules made with 2-propanol became much smoother as the ungelled starch particles gelled upon contact with water (See FIG. 4, panel B). The small pores inside the granules disappeared and the granules resembled granules made with water only (See FIG. 4, panels C and D). Granules made with water only did not change in appearance after wetting (See FIG. 4, panels A and C)(Photomicrographs taken at 250x).

Granules made with 2-propanol adhered to each other as well as to the glass slide, whereas granules made only with water remained distinct and appeared similar to granules that had not been wetted.

2. Adherence

The effects of organic solvent on granule adherence are summarized in Table 1, below.

TABLE 1

| Solvent[a] | Mean % Loss of Granules from Slides[b] | | Average Mg Granules On Cotton Leaves Days After Appl. | |
|---|---|---|---|---|
| | | | 0 | 7 |
| Water | 100.0 | A | 15.5 A | 2.4 A |
| 2-propanol | 2.5 | F | 27.6 CD | 16.7 D |
| Methanol | 83.0 | B | 23.6 B | 7.1 B |
| Ethanol | 13.5 | DE | 28.2 D | 14.1 CD |
| n-butyl Alcohol | 10.5 | E | 28.8 D | 15.6 CD |
| Acetone | 39.5 | C | 25.9 BCD | 7.2 B |
| 1,4-Dioxane | 18.5 | D | 24.2 BC | 11.9 C |

[a]Granules were prepared by mixing 50 g Miragel ® with 35 ml water and 15 ml solvent.
[b]Means followed by same letter within a column are not significantly different (Least Significant Difference P < 0.05).

The data in Table 1 show that granules prepared with an organic solvent had enhanced adherence to cotton leaves when compared to granules made without such solvent, both initially (Day 0)(ANOVA, F=12.87; df=6,63; p<0.001) and after 7 days (ANOVA, F=10.49; df=6,63; p<0.001).

B. Effect of Starch Type on Granule Adherence

Granules were produced by admixing about 25 g of pregelatinized starch with 25 milliliters (ml) of an aqueous solvent comprising 25 ml water (A) or 17.5 ml of water and 7.5 ml of 2-propanol (B). After allowing the gelled mass to granulate, the mass was broken apart in a blender or crumbled to produce granules that passed 20 mesh but not 40 mesh (425 μm to about 850 μm). The adherence of formed granules to both glass microscope slides and leaves of cotton plants was determined in accordance with the procedures of Example 1.

Miragel®, a fully pregelatinized cornstarch was obtained from Staley Inc., Decatur, Ill. "Flour 961" (Illinois Cereal Mills, Paris, Ill.), pearl cornstarch (CPC International, Englewood Cliffs, N.J.), waxy cornstarch (American Maize Products, Hammond, Ind.), potato amylopectin and "Amylon 5" (National Starch and Chemical Co., New Jersey), and "Staco M" (Staley Inc.) were gelatinized using standard procedures well known in the art.

Briefly, about 100 g of starch was added to about 1 liter of water to form a mixture and the mixture cooked at about 80° C. for about 10 minutes to cause gelatinization. The mixture was cooled to about 50° C. Before retrogradation occurred, the gelatinized starch was recovered by precipitating the cooled mixture with about 3 liters of 95 percent (v/v) ethanol in a blender. The precipitate was collected by filtration, washed with absolute ethanol and dried.

The effect of starch type on granule adherence is summarized in Table 2, below.

TABLE 2

| Starch Type | Solvent | % Loss Of Granules from Slides | Granules (mg) on Cotton Leaves (Days After Application) | |
|---|---|---|---|---|
| | | | 0 | 7 |
| Amylon 5 | A | 100 | 19.5 | 0.0 |
| | B | 100 | 22.1 | 0.1 |
| Flour 961 | A | 100 | 18.13 | 1.29 |
| | B | 10 | 24.15 | 14.54 |
| Waxy | A | 75 | 27.3 | 4.9 |
| | B | 40 | 29.0 | 20.6 |

TABLE 2-continued

| Starch Type | Solvent | % Loss Of Granules from Slides | Granules (mg) on Cotton Leaves (Days After Application) 0 | 7 |
|---|---|---|---|---|
| Pearl | A | 100 | 25.0 | 7.7 |
|  | B | 9 | 27.7 | 18.5 |
| Staco M | A | 100 | 27.3 | 1.7 |
|  | B | 100 | 27.0 | 16.5 |
| Potato | A | 100 | 21.04 | 0.7 |
| Amylopectin | B | 50 | 25.48 | 21.41 |
| Miragel ® | A | 100 | 27.0 | 9.5 |
|  | B | 2.5 | 25.9 | 15.3 |

The data show that 2-propanol increased the adherence of granules to glass slides with all starches examined (analysis of variance, F=1268.25, df=1,56, p<0.001). There was a significant effect on adherence due to starch type (F=142.88, df=6,56, P<0.001). Furthermore, a significant interactive effect (F=102.52, df=6,56, P<0.001) indicated that not all starches behaved the same with respect to addition of 2-propanol. By way of example, granules made with Miragel® and gelatinized pearl starch exhibited the greatest level of adherence to glass slides when made with 2-propanol. Granules made from gelatinized "Amylon 5" or gelatinized "Staco M" showed no adherent properties on glass when mixed with 2-propanol. Other starch products (gelatinized waxy and gelatinized potato amylopectin) demonstrated intermediate properties in relation to adherence.

Starch type also affected the adherence of granules to cotton leaves, when granules made with and without 2-propanol were compared (analysis of variance, F=30.89, df=6,126, P<0.001). Granules made with gelatinized "Amylon 5" did not adhere well. Granules made with Miragel®, gelatinized waxy, and gelatinized pearl starch all adhered equally well. As with glass slides, a significant interaction occurred (analysis of variance, F=15.26, df=4,90, P<0.001) because 2-propanol had a large influence over adherence of all starch granules, except those made with gelatinized "Amylon 5".

Similar to results of the glass slide assays, 2-propanol had a significant effect on adherence of various starch granules after 7 days (analysis of variance, F=342.51, df=1,126, P<0.001).

C. Bioassay with *B. thuringiensis*

To test the effect of 2-propanol use on survival of insecticidal activity of *B. thuringiensis,* granules were prepared in accordance with the procedures of Example 2A with a 30 percent (v/v) solution of 2-propanol except that *B. thuringiensis* technical powder (supplied by Abbott Laboratories) was added at the rate of 1600 International units per mg of dry ingredients. As controls, granules were prepared with water alone and both formulations were prepared without *B. thuringiensis.* Those four granule types were then assayed for insecticidal activity against European corn borer (*Ostrinia nubilalis* Hubner [Lepidoptera:Pyralidae]) neonates.

Assays were initiated by incubating 100 mg of granules in 2 ml distilled water containing 2 mg α-amylase at 37° C. for 1 hour. The suspension was diluted to about 8 ml with water and then homogenized for 10 seconds in a Virtishear tissue homogenizer (Virtis) at full power. Two ml of green food coloring were then added.

Sixty neonate corn borers were allowed to feed on droplets of the suspension (Hughes & Wood 1981) and were then transferred individually to plastic cups containing artificial diet. Percent mortality was calculated 2 days later. The data from that study are summaried in Table 3, below.

TABLE 3

| Formulation Ingredients | Bt IU/mg | Percent Mortality* Test 1 | Test 2 |
|---|---|---|---|
| Miragel ® water | 1600 | 48 | 48 |
| Miragel ® water 2-Propanol | 1600 | 52 | 42 |
| Miragel ® water | 0 | 0 | 0 |
| Miragel ® water 2-propanol | 0 | 1.7 | 0 |

*based on 60 insects/formulation

Granules made with *B. thuringiensis* and 2-propanol showed little or no reduction in activity as measured by percent mortality of *O. nubilalis* (52%, 42% in two tests) when compared to granules made in the same manner but without 2-propanol (48%).

D. Field Trapping Test

Starch granular formulations were tested to determine how well they attracted the Western corn rootworm, *Diabrotica virgifera virgifera* LeConte. All granules were made with pregelatinized pearl starch, water, 2-propanol, carbaryl (an insecticide), and buffalo gourd root powder, (*Curcurbita foetedissima* H.B.K., a feeding stimulant); p-methoxycinnamaldehyde (PMCn; Schweizerhall, Inc., South Plainfield, N.J.) was used in some formulations as an attractant.

Granules were prepared by admixing about 30 g of pregelatinized pearl starch with about 30 ml of a 30 percent (v/v) solution of 2-propanol. Before gelatinization, carbaryl (2 percent AI/dry wt) and dried, powdered, root of buffalo gourd (*Cucurbita foetidissima* H.B.K.) (5 percent wt/wt) were added.

To determine if a volatile attractant could also be encapsulated and yet be released over a period of time, p-methoxycinnamaldehyde (Schweizerhall, Inc. South Plainfield, N.J.), shown by Lampman & Metcalf (1988) to be an attractant for *D. v. virgifera,* was added to the formulation in one of two ways: the attractant was added to the dry ingredients prior to gelling, or granules previously made were soaked in a solvent containing the attractant.

To determine the effect of attractant concentration on granule attractancy, three different concentrations (about 0.1, 1.0 and 10.0 percent of dry wt.) were used. Actual concentrations of a p-methoxycinnamaldehyde were determined by soaking the granules in 50% ethanol and measuring absorption at 320 nm in a Beckman DU-50 spectrophotometer. Following formulation, 100 mg granules were placed in vial traps (Shaw et al., 1984) with solid bottoms (Lance, 1988) and placed at ear height in field corn on Aug. 7, 1990. This experiment was set up in a randomized complete block design with five blocks. A block consisted of a row of corn with vials spaced approximately 10 meters apart.

Blocks were separated by 10 rows. Traps were sampled 3, 6, 9 and 12 days after placement in the field. Additionally, enough traps were initially established so that half of the vials could receive fresh granules after 6 days. Therefore a total of 14 traps were in each block; three with encapsulated p-methoxycinnamaldehyde and not changed after 6 days, three with attractant soaked into the granule and not changed after 6 days, and the same six types of granules but changed after 6 days. Two treatments of control granules without attractant were also placed in the field; one treatment was changed after 6 days, the other was not.

There were 14 treatments replicated 5 times each. Analysis of variance was conducted in a 4×14 factorial design with day and treatment as main effects. Contrasts were then used to determine daily relative effects of changing the granules, the method of attractant addition, and the concentration of attractant. Mean numbers of beetles caught for each 3 day period (Table 4, hereinafter) were subjected to the statistical contrasts presented in Table 5, hereinafter. Results of these analyses are presented in Table 6, hereinafter.

Results for each day showed there were fewer beetles trapped in vials with granules containing no attractant than in vials baited with attractant. These results suggest a sustained release of p-methoxycinnamaldehyde over the 12 day period (Contrast 1). Except for the first 3 day period, there was no effect due to the position of attractant (i.e., soaked vs. encapsulated) or whether or not granules were changed (Contrasts 2, 3, 6, 7, 8, 9, 10, 11). There was a significant linear relationship with respect to concentration of attractant indicating a dose effect (Contrast 4, 5, 12, 13). There was a significant effect due to the day of capture ($F=92.5$, $df=3,195$, $P<0.001$) because more beetles were caught during the later sampling periods (Table 4). This represents an increase in the overall population because rootworm emergence continued through the month of August.

TABLE 4

| Trap No. | %PMCn Conc.[a] | PMCn Pos[b] | Granules Changed After 6d | Mean Beetles/Trap Day 3 | 6 | 9 | 12 |
|---|---|---|---|---|---|---|---|
| 1 | 0 | — | No | 3.6 | 13.2 | 21.8 | 69.8 |
| 2 | 0.095 | enc | No | 10.6 | 30.6 | 26.6 | 71.2 |
| 3 | 0.74 | enc | No | 26.6 | 32.8 | 31.4 | 62.6 |
| 4 | 6.85 | enc | No | 45.6 | 34.0 | 66.4 | 101.2 |
| 5 | 0.095 | soaked | No | 31.8 | 22.4 | 28.2 | 71.0 |
| 6 | 0.82 | soaked | No | 48.6 | 50.8 | 55.0 | 77.0 |
| 7 | 8.6 | soaked | No | 42.0 | 48.6 | 68.8 | 100.4 |
| 8 | 0 | — | Yes | 7.4 | 16.8 | 21.8 | 64.2 |
| 9 | 0.095 | enc | Yes | 11.4 | 21.2 | 34.0 | 91.4 |
| 10 | 0.74 | enc | Yes | 25.8 | 24.2 | 49.4 | 89.0 |
| 11 | 6.85 | enc | Yes | 41.4 | 35.0 | 56.4 | 87.6 |
| 12 | 0.095 | soaked | Yes | 26.0 | 24.8 | 30.6 | 58.8 |
| 13 | 0.82 | soaked | Yes | 41.4 | 22.2 | 49.4 | 67.6 |
| 14 | 8.6 | soaked | Yes | 57.6 | 42.6 | 65.8 | 107.8 |
| Total Beetles Captured | | | | 2099 | 2096 | 3028 | 5589 |

[a] p-Methoxycinnamaldehyde was assayed by soaking 10 mg granules for 1 hour in 100 ml 50% ethanol and then reading absorbance at 320 nm. Readings were compared to standard curve.
[b] p-Methoxycinnamaldehyde was added to the formulations prior to gelatinization (enc) or granules previously prepared were soaked in solvent containing PMCn.

TABLE 5

CONTRASTS USED TO DETERMINE DIFFERENCES AMONG TREATMENT COMBINATIONS (df = 1,52) FOR EACH DAY

| CONTRAST # | MEANS COMPARED |
|---|---|
| 1 | Controls vs all others |
| 2 | Enc vs soaked, granules not changed |
| 3 | Enc vs soaked, granules changed. |
| 4 | Linear contrast concentration, enc |
| 5 | Linear contrast concentration, soaked |
| 6 | Granules changed vs not changed, concentration ≈ 0.1% |
| 7 | Granules changed vs. not changed, concentration ≈ 1.0% |
| 8 | Granules changed vs not changed, concentration ≈ 10.0% |
| 9 | Enc vs soaked, concentration ≈ 0.1% |
| 10 | Enc vs soaked, concentration ≈ 1.0% |
| 11 | Enc vs soaked, concentration ≈ 10.0% |
| 12 | Linear contrast concentration, granules not changed |
| 13 | Linear contrast concentration, granules changed |

TABLE 6

SUMMARY OF RESULTS FROM CONTRASTS IN TABLE 5 FOR EACH DAY OF TRAP COUNTS

| Con-trast | DAY 3 | | 6 | | 9 | | 12 | |
|---|---|---|---|---|---|---|---|---|
| | F[a] | Pr > F | F | Pr > F | F | Pr > F | F | Pr > F |
| 1 | 35.75 | 0.00 | 13.6 | 0.00 | 34.49 | 0.00 | 4.24 | 0.04 |
| 2 | 6.68 | 0.01 | 2.51 | 0.12 | 4.08 | 0.05 | 0.32 | 0.57 |
| 3 | 9.17 | 0.00 | 0.36 | 0.55 | 0.19 | 0.66 | 2.06 | 0.16 |
| 4 | 42.66 | 0.00 | 9.43 | 0.00 | 53.34 | 0.00 | 6.35 | 0.01 |
| 5 | 56.74 | 0.00 | 27.69 | 0.00 | 81.47 | 0.00 | 15.21 | 0.00 |
| 6 | 0.16 | 0.69 | 0.31 | 0.58 | 0.77 | 0.38 | 0.17 | 0.68 |
| 7 | 0.41 | 0.52 | 8.84 | 0.00 | 1.23 | 0.27 | 0.78 | 0.38 |
| 8 | 0.83 | 0.37 | 0.16 | 0.69 | 1.36 | 0.25 | 0.10 | 0.75 |
| 9 | 8.19 | 0.00 | 0.13 | 0.72 | 0.03 | 0.87 | 2.90 | 0.09 |
| 10 | 9.03 | 0.00 | 1.62 | 0.21 | 4.47 | 0.04 | 0.13 | 0.72 |
| 11 | 1.01 | 0.32 | 3.11 | 0.08 | 1.12 | 0.29 | 1.02 | 0.32 |
| 12 | 33.08 | 0.00 | 17.28 | 0.00 | 51.97 | 0.00 | 6.26 | 0.02 |
| 13 | 35.18 | 0.00 | 7.63 | 0.00 | 40.35 | 0.00 | 8.01 | 0.01 |

[a] df = 1,52

Example 3

Studies with Inorganic Salt

A. Effects of Inorganic Salt Type on Granule Adherence

Granules were prepared by admixing about 30 g of Miragel® with a mixture of one or more inorganic salts and water. As mixing progressed, discrete granules formed. Those granules were tested for adherence to glass microscope slides in accordance with the procedures of Example 1. The results of those studies are summarized in Table 7, below.

TABLE 7

| Salt Type | Salt(g) | Water (ml) | Mixture (ml) | % Loss From Slide |
|---|---|---|---|---|
| $CaCl_2$ | 90 | 60 | 8 | 12 |
| KI | 20 | 20 | 12 | 21 |
| $(NH_4)_2SO_4$ | 20 | 40 | 12 | 48 |
| $Na_2SO_4$ | 18 | 40 | 10 | 21 |
| $Na_2CO_3$ | 20 | 50 | 14 | 19 |

TABLE 7-continued

| Salt Type | Salt(g) | Water (ml) | Mixture (ml) | % Loss From Slide |
|---|---|---|---|---|
| $Na_2SO_4$ + $Na_2CO_3$ | 10 | 40 | 10 | 5 |

B. Adherence of Granules to Cotton Leaves

Granules were prepared by admixing about 26 g of starch with about 7 ml of an aqueous solution made by dissolving about 45 g $CaCl_2$—$H_2O$ in 30 ml water. As a control, granules were prepared with 25 ml water and 25 g Miragel®. Approximately 30 mg of granules were applied to each of 30 prewetted cotton leaves.

At 1, 7, or 14 days after application, granules were collected from each of 10 leaves per treatment and weighed to determine adherence over time. Additionally, water was applied to each leaf disk three times between each of the three sampling periods.

Where the starch was Miragel®, all of granules made with calcium chloride (30 mg) were present on day 1, whereas only 24 mg of granules made with water were present. After 7 days, 22 mg of calcium chloride granules remained whereas only 11 mg of water granules were present. After 14 days, 13 mg of calcium chloride granules remained whereas only 3 mg of water granules were present.

Where the starch was pregelatinized corn flour 961, 21 mg of granules made with calcium chloride and 25 mg of granules made with water were recovered on day 1. After 7 days the average recovery was 20 mg and 3 mg for calcium chloride and water granules, respectively.

C. Effect of Granule Size

To test the effect of particle size on adherence to cotton leaves, granules were prepared by admixing about 26 g of starch with about 7 ml of an aqueous solution made by dissolving about 45 g $CaCl_2$—$2H_2O$ in 30 ml water and then sieved with wire mesh to the desired size ranges. The adherence of granules to cotton plant leaves was determined in accordance with the procedures of Example 1 after 1 and 7 days.

26 Mg and 20 mg of granules that passed 20 mesh but not 40 mesh (+20–40) were recovered after 1 and 7 days, respectively. 20 and 16 mg of +10–20 sized granules were collected on days 1 and 7 respectively.

In another study, granules were made as above except that pregelatinized flour 980 (supplied by Illinois Cereal Mills) and a lower concentration of $CaCl_2$ (30 g $CaCl_2$—$2H_2O$ in 30 ml water) were used. Those granules were then sieved with wire mesh to the desired size ranges. The adherence of granules to cotton plant leaves was determined in accordance with the procedures of Example 1 after 1 and 7 days.

23 Mg and 12 mg of +16–20 sized granules were collected after 1 and 7 days respectively while 17 mg and 8 mg of +10–16 granules were collected for the same time periods.

The data from those studies show that granules made with calcium chloride adhered to cotton foliage whereas granules made with water alone washed off. Further, in general, smaller granules adhered better than larger granules and granules made with flour 961 adhered better than granules made with flour 980.

D. Bioassays with European Borers

Studies were designed to test the actual acceptance of granules made and used in accordance with a process of the present invention. Granules were prepared with Miragel®, corn flour 961 and $CaCl_2$ in accordance with the procedures set forth above in section C except that Bt was added to the liquid portion prior to adding the solids. Bt activity is measured in international units so sufficient Bt was added to achieve the desired activity of the granule. Some granules were prepared with Coax®, a commercially available feeding stimulant to which corn borer larvae respond favorably.

Granules were then applied to wet cotton foliage in a premarked area of 33 $cm^2$ by carefully sprinkling granules from a glycine envelope. After drying, the leaf area was removed and placed in a 9 cm plastic Petri dish containing 10 neonate (newly hatched) corn borer larvae. Three days later the dishes were opened and percent mortality of the larvae was obtained. 10 replicates were conducted for each treatment. The results of those studies are summarized in Table 8, below, in which bold lines separate individual experiments.

TABLE 8

| Starch | Additive | Granules(mg) on Leaf | Bt IU/mg | Percent Mortality |
|---|---|---|---|---|
| Miragel ® | None | 30 | 1600 | 80 |
| Flour 961 | None | 30 | 1600 | 85 |
| Flour 961 | None | 30 | 0 | 11 |
| Miragel ® | None | 30 | 1600 | 69 |
| Flour 961 | None | 30 | 1600 | 56 |
| Flour 961 | None | 30 | 0 | 29 |
| Miragel ® | None | 30 | 0 | 1 |
| Miragel ® | Coax ® | 30 | 0 | 2 |
| Miragel ® | None | 30 | 1600 | 59 |
| Miragel ® | None | 20 | 1600 | 50 |
| Miragel ® | None | 10 | 1600 | 45 |
| Miragel ® | Coax ® | 30 | 1600 | 89 |
| Miragel ® | Coax ® | 20 | 1600 | 98 |
| Miragel ® | Coax ® | 10 | 1600 | 70 |
| Miragel ® | Coax ® | 5 | 1600 | 82 |
| Miragel ® | None | 30 | 0 | 10 |
| Miragel ® | Coax ® | 30 | 0 | 5 |
| Miragel ® | None | 30 | 1600 | 89 |
| Miragel ® | None | 20 | 1600 | 69 |
| Miragel ® | None | 10 | 1600 | 79 |
| Miragel ® | None | 5 | 1600 | 67 |
| Miragel ® | Coax ® | 30 | 1600 | 90 |
| Miragel ® | Coax ® | 20 | 1600 | 93 |
| Miragel ® | Coax ® | 10 | 1600 | 92 |
| Miragel ® | Coax ® | 5 | 1600 | 76 |
| Miragel ® | None | 10 | 0 | 4 |
| Miragel ® | None | 10 | 1600 | 26 |
| Miragel ® | None | 10 | 800 | 18 |
| Miragel ® | None | 10 | 400 | 16 |
| Miragel ® | Coax ® | 10 | 1600 | 54 |
| Flour 961 | None | 10 | 0 | 6 |
| Flour 961 | None | 10 | 1600 | 53 |
| Flour 961 | None | 10 | 800 | 45 |
| Flour 961 | None | 10 | 400 | 23 |
| Flour 961 | Coax ® | 10 | 1600 | 49 |
| Flour 961 | None | 10 | 0 | 0 |
| Flour 961 | None | 10 | 1600 | 31 |
| Flour 961 | None | 10 | 800 | 23 |
| Flour 961 | Coax ® | 10 | 0 | 3 |
| Flour 961 | Coax ® | 10 | 1600 | 44 |
| Flour 961 | Coax ® | 10 | 800 | 39 |
| Flour 961 | None | 10 | 0 | 0 |
| Flour 961 | None | 10 | 1600 | 23 |
| Flour 961 | None | 10 | 800 | 29 |
| Flour 961 | None | 10 | 400 | 11 |
| Flour 961 | Coax ® | 10 | 0 | 2 |
| Flour 961 | Coax ® | 10 | 1600 | 36 |
| Flour 961 | Coax ® | 10 | 800 | 32 |
| Flour 961 | Coax ® | 10 | 400 | 24 |
| Flour 961 | Coax ® | 20 | 0 | 1 |
| Flour 961 | None | 20 | 400 | 8 |
| Flour 961 | None | 20 | 1600 | 28 |
| Flour 961 | Coax ® | 20 | 400 | 15 |
| Miragel ® | Coax ® | 20 | 1600 | 39 |
| Miragel ® | Coax ® | 20 | 0 | 0 |
| Miragel ® | None | 20 | 400 | 15 |
| Miragel ® | None | 20 | 1600 | 32 |

TABLE 8-continued

| Starch | Additive | Granules(mg) on Leaf | Bt IU/mg | Percent Mortality |
|---|---|---|---|---|
| Miragel ® | Coax ® | 20 | 400 | 66 |
| Miragel ® | Coax ® | 20 | 1600 | 79 |

Granules made with calcium chloride and Coax® were more effective than granules made without Coax®. Generally, higher quantities of granules killed more insects and granules with higher levels of *Bt* also killed more larvae.

Granules made with Flour 961 clumped, even before application leading to less even dispersion of the granules. Such clumping likely resulting in lower mortality because insects are not as likely to discover fewer clumps as compared to an even distribution of granules on the leaf surface.

E. Feeding Preference

These studies were designed and conducted to determine whether corn borers would feed preferentially on one type of granule when given a choice of two. Granules were prepared with Miragel®, corn flour 961 or corn flour 980 as disclosed in section C, above. Feeding preference was determined in accordance with standard procedures well known in the art (Bartlett et al.). The results of those studies are presented below in Table 9, in which individual experiments are separated by a bold line.

TABLE 9

| Granule 1 Type | Larvae # | Granule 2 Type | Larvae # | Preferred Granule |
|---|---|---|---|---|
| Miragel ® | 6 | Miragel-Coax ® | 30 | Miragel-Coax ® |
| Miragel ® | 6 | 961 | 20 | 961 |
| Miragel ® | 11 | 961-Coax ® | 22 | 961-Coax ® |
| Miragel ® | 7 | 980 | 20 | 980 |
| Miragel ® | 5 | 980-Coax ® | 28 | 980-Coax ® |
| Miragel-Coax ® | 5 | 961 | 15 | 961 |
| Miragel-Coax ® | 14 | 961-Coax ® | 34 | 961-Coax ® |
| Miragel-Coax ® | 15 | 980 | 43 | 980 |
| Miragel-Coax ® | 6 | 980-Coax ® | 25 | 980-Coax ® |
| 961 | 11 | 961-Coax ® | 13 | No pref |
| 961 | 11 | 980 | 29 | 980 |
| 961 | 10 | 980-Coax ® | 26 | 980-Coax ® |
| 961-Coax ® | 17 | 980 | 12 | 961-Coax ® |
| 961-Coax ® | 25 | 980-Coax ® | 24 | No pref |
| 980 | 12 | 980-Coax ® | 29 | 980-Coax ® |

The data show that granules made with either flour 961 or flour 980 were highly preferred when larvae were given a choice against granules made with Miragel®. Larvae even preferred granules made with either flour when given a choice against granules made with Miragel® and Coax® suggesting that the protein component in the flour is a better feeding stimulant than the ingredients of Coax®. Larvae showed no or slight preference when given choice between granules made with either flour when Coax® was also present but when Coax® was absent, larvae preferred flour 980.

F. Bioassay of Granules in Corn

Granules were prepared either by admixing (1) about 26 g of corn flour 961 with about 7 ml of an aqueous solution made by dissolving about 45 g $CaCl_2$—$2H_2O$ in 30 ml water or (2) about 26 g of pregelatinized flour 980 with about 7 ml of an aqueous solution made by dissolving about 30 g $CaCl_2$—$2H_2O$ in 30 ml water. Granules were applied to the whorls of greenhouse-grown corn plants. Either egg masses (2/plant) or larvae (25/plant) were then applied to the corn plant. 7 days later, plants were dissected and live larvae were counted.

The data from those studies are presented below in Table 10, in which individual experiments are separated by bold lines.

TABLE 10

| Flour | Particle Size | Mg of Granule | Bt IU/mg | Insect Stage | No. Surviving |
|---|---|---|---|---|---|
| 961 | +20–40 | 150 | 0 | egg | 9 |
| 961 | +10–20 | 150 | 0 | egg | 12 |
| 961 | +20–40 | 150 | 1600 | egg | 2 |
| 961 | +10–20 | 150 | 1600 | egg | 2 |
| 961 | +20–40 | 150 | 800 | egg | 2 |
| 961 | +10–20 | 150 | 800 | egg | 3 |
| 961 | +10–16 | 150 | 0 | larvae | 12 |
| 980 | +10–16 | 150 | 0 | larvae | 13 |
| 961 | +10–16 | 150 | 800 | larvae | 3 |
| 980 | +10–16 | 150 | 800 | larvae | 4 |
| 980 | +16–20 | 150 | 0 | larvae | 8 |
| 980 | +10–16 | 150 | 0 | larvae | 9 |
| 980 | +16–20 | 150 | 800 | larvae | 2 |
| 980 | +10–16 | 150 | 800 | larvae | 2 |
| 980 | +16–20 | 150 | 400 | larvae | 3 |
| 980 | +10–16 | 150 | 400 | larvae | 2 |
| 980 | +10–16 | 150 | 0 | larvae | 11 |
| 980 | +10–16 | 150 | 100 | larvae | 5 |
| 980 | +10–16 | 150 | 800 | larvae | 3 |

Granules were all extremely effective against corn borer larvae within the whorl of the plant. Granules tended to concentrate within the whorl where corn borers actively feed. Therefore it is highly likely that the larvae would locate and feed on the granules or ingest water contaminated by *Bt* that had washed off the outside of the granules (especially those granules made with flour 980). No significant differences were observed within the various treatments containing *Bt*.

Example 4

Studies with Organic Solvent and Inorganic Salt

A. Adherence to Glass Slides

Granules were prepared by admixing about 30 g Miragel® with a water-miscible organic solvent and an aqueous solvent comprising an inorganic salt. Granules were prepared from the gelled mass in accordance with the procedures of Example 2. The adherence of formed granules was determined in accordance with the procedures of Example 1. Summary data from that study are presented below in Table 11.

TABLE 11

| Salt Type(g) | Solvent (ml) | Water (ml) | Mixture (ml) | % Loss from Slide |
|---|---|---|---|---|
| $FeCl_3$(10) | Acetone (5) | 15 | 12 | 12 |
| $(NH_4)_2SO_4$(10) | IPOH (10) | 40 | 14 | 6 |

The data in Table 9 show that granules prepared using a water-miscible organic solvent [Acetone or isopropyl alcohol (IPOH)] and an inorganic salt [$FeCl_3$ or $(NH_4)_2SO_4$)] adhere to glass slides.

B. Adherence to Cotton Leaves

Granules were prepared with Miragel® (30 g), an inorganic salt and a water-miscible organic solvent in accordance with the procedures of Example 2 and their adherence to cotton leaves determined in accordance with the procedures of Example 1. Summary data from those studies are presented in Table 12, below.

TABLE 12

| Salt (g) | Organic Solvent (ml) | Water (ml) | Mixture (ml) | 1 Day | 7 Days |
|---|---|---|---|---|---|
| $(NH_4)_2SO_4$ (10) | 2-propanol (10) | 40 | 14 | 28.97* | 14.85* |
| $(NH_4)_2SO_4$ (10) $Na_2SO_4$ (10) | None | 40 | 10 | 25.94 | 18.28 |
| KI (20) | None | 20 | 10 | 24.90 | 17.43 |
| $FeCl_3$ (10) | Acetone (5) | 15 | 12 | 20.99 | 12.07 |
| $(NH_4)_2SO_4$ (15)** | None | 4 | 0 | 11.78 | 0.62 |
| $(NH_4)_2SO_4$ (20) | None | 35 | 10 | 22.83 | 8.69 |
| None | 2-propanol (50) | 0 | 0 | 25.59 | 15.50 |
| $(NH_4)_2SO_4$ (20) anhydrous | None | 40 | 10 | 21.50 | 12.84 |
| $Na_2CO_3$ (20) | None | 50 | 14 | 22.43 | 14.78 |

* granules remaining (mg)
** $(NH_4)_2SO_4$ was powdered and added directly to Miragel 200

The data in Table 12 show that granules prepared with a water-miscible organic solvent, an inorganic salt or a mixture thereof adhere to a plant foliar surface.

C. Bioassay with *B. thuringiensis*

Granules were prepared with Miragel®, the entomopathogen *Bacillus thuringiensis* (*Bt*), and various formulations of water, water-miscible organic solvent and inorganic salt. Granules were then hydrolyzed with amylase enzyme and fed to neonate *Ostrinia nubilalis* as described in Example 3. Six different granule formulations were prepared and studied.

In formulation 1, 43 g Miragel® was admixed with 35 ml of a solution of 30 percent(v/v) 2-propanol. 1 G of *Bt* technical powder (from Abbott Laboratories 68,900 IU/mg) was then coated onto the outside of the granules.

In formulation 2, 43 g Miragel® was admixed with 43 ml of a solution of 30 percent (v/v) 2-propanol. 1 g of *Bt* technical powder (from Abbott Laboratories 68,900 IU/mg) was then coated onto the outside of the granules.

In formulation 3, 43 g Miragel® was admixed with 1 g of *Bt* and then with 43 ml of a 30 percent (v/v) solution of 2-propanol. This resulted in the *Bt* being evenly dispersed throughout the granule.

In formulation 4, 90 g of $CaCl_2.2H_2O$ was dissolved in 60 ml water. 4 ml of this solution was admixed with 30 g Miragel®. An additional 4 ml of a $CaCl_2$ solution was then mixed to form granules. 975 Mg *Bt* was then coated onto the granules.

In formulation 5, 975 mg of *Bt* was admixed with 30 g Miragel®. About 8 ml of a $CaCl_2$ solution (90 g $CaCl_2$ $2H_2O$ was dissolved in 60 ml water) was added to the starch-*Bt* mixture.

In formulation 6, 30 g of Miragel® was admixed with *Bt* (1600 IU/mg) and then added to 30 ml water. Several hours later, the mass was in a Waring blender.

The results of those studies are summarized in Table 13, below.

TABLE 13

| FORMULATION # | % MORTALITY* |
|---|---|
| 1 | 47 |
| 2 | 50 |
| 3 | 55 |
| 4 | 52 |
| 5 | 63 |
| 6 | 42 |
| Control | 0 |

*Based on 60 insects/formulation.

The data in Table 13 show that the insecticidal activity of the entomopathogen *Bt* was not affected when incorporated and used in accordance with a process of the present invention.

Example 5
Studies with Other Water Dispersants
A. Sugars

A sugar solution was prepared by admixing about 20 g water with about 80 g of a sugar (molasses, sucrose or Staley dextrin 200). About 30 g of flour 961 was added to about 8 ml of the sugar solution and the resulting admixture blended. Formed granules were then dried to remove excess water. Granule adherence to glass slides and cotton leaves was determined in accordance with the procedures of Example 1.

61.2, 63 and 35.8 percent of granules made with sucrose, molasses and Staley dextrin 200, respectively, adhered to glass slides following four wash/dry cycles.

13.9, 14.3, and 18.51 Mg of granules made with sucrose, molasses, and Staley dextrin 200, respectively, remained on cotton leaf surfaces after seven days in the greenhouse.

15 g pregelatinized Flour 961 was mixed with 1.5 g 2,4-D salt (2,4-dichlorophenoxyacetate sodium salt) and 4 g molasses (74% solids) in a mortar and pestle. Formulations were also prepared substituting 2,4,-D with 2,4-D ester (2,4-dichlorophenoxyacetate isopropyl ester), metolachlor (2-Chloro-N-(2-ethyl-6-methylphenyl)-N-(2-methoxy-1-benzenedicarboxylate), diazinon (0,0-diethyl 0-[6-methyl-2-(1-methylethyl)-4-pyrimidinyl]phosphorothioate), or carbaryl (1-naphtalenyl methylcarbamate). In another example, 11 g Dimilin (N-{[(4-chlorophenyl)amino}carbonyl]-2,6-difluorobenzamide) was suspended in 50 ml 2-propanol and 100 ml water and mixed with 200 g Miragel®. All the above samples adhered well to prewetted glass microscope slides.

B. Desiccated Organismic Matter
1. Plant Leaf Method

5 G of fresh plant leaves was admixed with 15 g pregelatinized flour 961 or Miragel® in a Waring blender. The plant tissue provided adequate moisture to gel the flour and form granules. Following drying, 16 g material was recovered. The adherence of formed granules to glass slides and cotton leaves was determined as above.

In the glass slide assay, adherence was 90.3 percent for granules made with Miragel® and corn leaf, 91.6 percent for granules made with Miragel® and cotton leaves, 83.1 percent for granules made with flour and horseradish leaves and 75.6 percent for granules made with flour and cotton leaves.

22 mg of granules made with flour and cotton leaves remained on cotton leaf surfaces after 7 days.
2. Insect Method 5 G frozen grasshoppers either infected with entomopoxvirus or not infected (ca 12 infected grasshoppers or 5 noninfected) was admixed with 15 g pregelatinized flour 961 in a Waring blender. The moisture in the grasshoppers was sufficient to cause gelling and granule formation. Following drying, 18 g granules were recovered. The adherence of formed granules to glass slides and cotton leaves was determined as above.

Twenty-six percent of granules placed on glass slides were retained after 4 wash/dry cycles, whereas 16.3 mg granules remained on cotton leaf surfaces 7 days after the application of 30 mg of granules/leaf.

Approximately 30 3rd–4th instar grasshoppers were placed in cylindrical mylar tubes (30 cm long, 10 cm diameter) containing 1 g of one of four test formulations, and approximately 20 g fresh rye seedling leaves as described below.

1. Granules prepared with entomopoxvirus infected grasshoppers.
2. Granules prepared with non-infected grasshoppers.
3. Entomopoxvirus applied to wheat bran.
4. Control wheat bran.

After three days, granules were removed and provisions of fresh rye were provided for a period of 28 days. Grasshoppers were collected when they died and all grasshoppers were examined for virus infection using standard techniques.

Results from those studies are summarized below in Table 14.

TABLE 14

| Formulation No. | Grasshoppers Recovered | Grasshoppers Infected | % Infection |
|---|---|---|---|
| 1. | 66 | 63 | 95 |
| 2. | 77 | 1 | ≈1 |
| 3. | 62 | 56 | 90 |
| 4. | 84 | 3 | 4 |

3. Water Absorbent Polymer

Five g of water was absorbed by 0.25 g of absorbent polymer of starch and hydrolyzed acrylonitrile and added portion wise to 20 g of flour 961 in a Waring blender. Granules, which formed during the mixing process, were dried at room temperature. The adherence of formed granules to glass slides and cotton leaves was determined as above.

87 Percent of granules placed on glass slides were retained after 4 wash/dry cycles. 21.02 Mg of granules remained on cotton leaf surfaces 7 days after the application of 30 mg of granules/leaf.

4. Anhydrous $CaCl_2$

Pregelatinized flour 961 was admixed with sieved anhydrous $CaCl_2$ (pass 40 mesh) and blended to form a dust-like admixture with no discernable granules. The weight percent ratio of starch to $CaCl_2$ varied from about 8:2 to about 39:1. The adherence of formed granules to glass slides and cotton leaves was determined in accordance with a modification of the procedures of Example 1.

Instead of prewetting the glass slides or plant leaves, the dust was applied directly to dry surfaces and allowed to hydrate from the atmosphere. Then the surfaces were washed in accordance with previous procedures. After application to dry leaves, the $CaCl_2$ likely pulls moisture from the air in sufficient quantity to wet the flour thus incorporating added ingredients directly on the leaf surface.

The adherence of this formulation to glass slides varied with the ratio of starch to $CaCl_2$. Retention on glass slides was 36.6 percent where that ratio was 8:2 ratio; 16.3 percent where that ratio was 9:1; 3 percent where that ratio was 19:1; and 5.1 percent where that ratio was 39:1.

The adherence of this formulation to cotton leaves also varied with the ratio of starch to $CaCl_2$. Retention on cotton leaves after 7 days was 14.3 mg where that ratio was 8:2 and 8.6 mg where that ratio was 19:1.

A procedure to examine the efficacy of the various formulations against European corn borer larvae on cotton leaf discs was developed. Granules were made with sugar, plant leaves, frozen insects, water absorbent polymer or anhydrous $CaCl_2$ as disclosed above with the exception that Bt was added to some granules. From 10 to 30 mg of granules were applied to a moistened 33 $cm^2$ disc premarked onto fully expanded cotton leaves grown in the greenhouse. The disc was then cut out of the leaf and placed in a plastic dish with 10 newly hatched corn borer larvae. The larvae were allowed to feed for three days after which the dish was opened and live and dead larvae were counted to obtain percent mortality. Results from that study are summarized in Table 15, below.

TABLE 15

| Starch | Dispersant | Bt IU/mg | Additive | Mg of Granules on leaf | Percent Mortality |
|---|---|---|---|---|---|
| Miragel ® | Water | 0 | None | 30 | 10 |
| Miragel ® | IPOH | 0 | None | 30 | 3 |
| Miragel ® | CaCl | 0 | None | 30 | 4 |
| Miragel ® | Water | 1600 | None | 30 | 4 |
| Miragel ® | IPOH | 1600 | None | 30 | 41 |
| Miragel ® | IPOH | 1600 | Coax ® | 30 | 71 |
| Miragel ® | CaCl | 1600 | None | 30 | 59 |
| Miragel ® | CaCl | 1600 | Coax ® | 30 | 89 |
| Flour 961 | CaCl | 0 | None | 30 | 11 |
| Flour 961 | CaCl | 1600 | None | 30 | 85 |
| Flour 961 | *CaCl(9:1) | 0 | None | 20 | 21 |
| Flour 961 | *CaCl(9:1) | 1600 | None | 20 | 60 |
| Flour 961 | *CaCl(8:2) | 0 | None | 20 | 0 |
| Flour 961 | *CaCl(8:2) | 1600 | None | 20 | 71 |
| Flour 961 | Cotton | 0 | None | 10 | 4 |
| Flour 961 | Cotton | 1600 | None | 10 | 70 |
| Flour 961 | Cotton | 1600 | Coax ® | 10 | 84 |
| Miragel ® | CaCl | 1600 | None | 10 | 26 |
| Miragel ® | CaCl | 1600 | Coax ® | 10 | 53 |
| Flour 961 | CaCl | 1600 | None | 10 | 54 |
| Flour 961 | CaCl | 1600 | Coax ® | 10 | 49 |

*Granules applied to dry leaves

Example 6

Studies With Coated Granules 20 g Pregelatinized flour 980 (a commercial corn flour from Illinois Cereal Mills), mesh size +10–16 was mixed with 570 mg Condor technical *Bacillus thuringiensis* (Bt) (from Ecogen) suspended in 7 ml of a salt solution made by mixing equal amounts (wt/wt) of $CaCl_2.2H_2O$ and water. This resulted in a coating of the flour with Bt. Twenty-six grams of +10–16 mesh material was recovered following drying at room temperature.

An average of 16.6 and 8.1 mg of granules was recovered from cotton leaves 1 and 7 days, respectively, after application. Leaves were rinsed with water a total of three times in the seven day period as in example 1B. Granules made with mesh size +16–20 resulted in the recovery of 23 mg and 12 mg, respectively, 1 and 7 days after application to cotton leaves.

Following the procedures of example 3F, granules made as above with or without Bt were applied to corn whorls and infested with European corn borer larvae. Seven days later, an average of 1.7 corn borers were counted on corn plants treated with Bt granules whereas an average of 13.8 corn borers were recovered from plants treated with non Bt granules.

To scale up this process, 900 g of flour 980, mesh size +16–20 was dry mixed with 100 g of the feeding stimulant Coax® and 6.9 g technical Bt in a planetary mixer. While mixing, 300 ml of the calcium chloride solution was added portion wise. The air dried product contained 400 IU units Bt/mg material and retained the original particle size of the flour without any grinding.

Granules can also be prepared using a combination of flour 980 and flour 961. 125 g flour 980 (+10–16) was mixed with 25 g flour 961 (+60 mesh). 15 ml of the calcium chloride solution containing 1.65 g technical Bt was added while mixing. Recovery of the +10–16 mesh particles was 168 g after air drying.

The data from those studies demonstrate another aspect of this invention that Bt can be coated onto flour particles that adhere to a plant surface.

Example 7

Adherence of Granules to Other Surfaces

Adherent granules were made with powdered anhydrous calcium chloride and flour 961 in a ratio of 2:1 as in Example 5B4 and applied to dry surfaces. Those particles adhered to animal hair, iron metals and aluminum foil.

Granules were prepared by mixing Flour 961 with calcium chloride solution as in Example 3B. Granules that were mesh size +20–40 were applied to the prewetted surfaces of animal hair, saran wrap, aluminum foil, waxed paper, and polypropylene. Granules adhered well to all those surfaces and resisted wash-off as before.

The foregoing examples illustrate particular embodiments of the present invention. It will be readily apparent to one of skill in the art that various modifications, alterations and changes can be made in those embodiments without departing from the true spirit and scope of the invention.

REFERENCES

The references listed below are incorporated herein by reference to the extent that they supplement, explain, provide a background for, or teach methodology, techniques, and/or compositions employed herein.

Reference 1. Dunkle, R. L., Shasha, B. S. (1988). Starch-encapsulated *Bacillus thuringiensis:* A potential new method for increasing environmental stability of entomopathogens. Environ. Entomol. 17:120–126.

Reference 2. Hughes, P. R., Wood, H. A. (1981). A synchronous peroral technique for the bioassay of insect viruses. J. Invertebr. Pathol. 37:154–159.

Reference 3. Koestler, R. C. (1980). Microencapsulation by interfacial polymerization techniques—agricultural applications, pp. 117–132. In A. F. Kydonieus [ed.] Controlled release technologies: methods, theory, and applications. CRC Press, Boca Raton.

Reference 4. Lampman, R. L., Metcalf, R. L. (1988). The comparative response of Diabrotica species (Coleoptera: Chrysomelidae) to volatile attractants. Environ. Entomol. 17:644–648.

Reference 5. Lance, D. R. (1988). Responses of northern and western corn rootworms to semiochemical attractants in corn fields. J. Chem. Ecol. 14:1177–1185.

Reference 6. Lance, D. R., Sutter, G. R. (1990). Field-cage and laboratory evaluations of semiochemical-based baits for managing western corn rootworm beetles (Coleoptera Chrysomelidae). J. Econ. Entomol. 83:1085–1090.

Reference 7. Lund, R. L. (1988). MSUSTAT Statistical Analysis Package, vers 4.1. Research and Development Institute. Bozeman, Mont.

Reference 8. McGuire, M. R., Shasha, B. S., Lewis, L. C., Bartelt, R. J., Kinney, K. (1990). Field evaluation of granular starch formulations of *Bacillus thuringiensis* against *Ostrinia nubilalis* (Lepidoptera: Pyralidae). J. Econ. Entomol. 83:2207–2210.

Reference 9. McGuire, M. R., Streett, D. A., Shasha, B. S. (1991). Evaluation of starch-encapsulation for formulation of grasshopper (Orthoptera: Acrididae) entomopoxviruses. J. Econ. Entomol., 84:1652–1656.

Reference 10. Meinke, L. J., Z B Mayo, & T. J. Weissling (1989). Pheromone delivery system: western corn rootworm (Coleoptera: Chrysomelidae) pheromone encapsulation in a starch borate matrix. J. Econ. Entomol. 82:1830–1835.

Reference 11. Metcalf, R. L. & Lampman, R. L. 1989. Cinnamyl alcohol and analogs as attractants for corn rootworms (Coleoptera:Chrysomelidae). J. Econ. Entomol. 82:1830–1625.

Reference 12. Raun, et al. (1966). Encapsulation as a technique for formulating microbial and chemical insecticides. J. Econ. Entomal. 59:620–622.

Reference 13. Shasha, et al. (1984). Starch-borate pesticides for slow release. J. Appl. Polym. Sci. 29:67–73.

Reference 14. Shasha, B. S. & M. R. McGuire (1991). Slow release formulations of pesticides. In D. G. Chasin & L. E. Bode, (eds), Pesticide formulations and application systems. American Society for Testing and Materials, Philadelphia.

Reference 15. Shaw, J. T., W. G. Ruesink, S. P. Briggs, & W. H. Luckmann (1984). Monitoring populations of corn rootworm beetles (Coleoptera: Chrysomelidae) with a trap baited with cucurbitacins. J. Econ. Entomol. 77:1495–1499.

Reference 16. Shotwell, R. L. (1944). Evaluation of baits and bait ingredients used in grasshopper control. USDA Tech. Bull. 793.

Reference 17. Trimnell, D. et al., (1982). Pesticide encapsulation using a starch-borate complex as wall material, J. of Applied Polymer Science, 27:3919–3928.

Reference 18. Trimnell, D. and Shasha, B. S. (1988) Entrapment of herbicides in starch for spray applications, J. Controlled Release 7:263–268.

Reference 19. Synek, J. (1983). Formulation, development, and application of an insecticide granule, pp. 123–131. In T. M. Kaneko & N. B. Akesson [eds.] Pesticide formulations and application systems: third symposium, ASTM STP 828. American Society for Testing and Materials, Philadelphia, 1983.

Reference 20. Vander Hooven, D. I. B. (1983). Corncob granules and pelleted carriers—new, controlled, safer methods of handling pesticides, pp. 132–140. In T. M. Kaneko & N. B. Akesson [eds.] Pesticide formulations and application systems: third symposium, ASTM STP 828. American Society for Testing and Materials, Philadelphia, 1983.

Reference 21. Weissling, T. J. & Meinke, L. J. 1991. Potential of starch encapsulated semiochemical/insecticide formulations for adult corn rootworm (Coleoptera: Chrysomelidae) control. J. Econ. Entomol. 84:601–609.

Reference 22. Wing, R. E. and Otey, T. H. (1983) Determination of reaction variables for the starch xanthine encapsulation of pesticides. J. Polym. Sci. Polym. Chem. Ed. 21:121–140.

What is claimed is:

1. A process of preparing an adherent starch-based granule incorporating a pest control agent, said process comprising the steps of:

(a) admixing, at a temperature of from about 5° C. to about 100° C., an effective incorporating amount of a pregelatinized starch, a pesticidally effective amount of said pest control agent, an effective dispersant amount of a water dispersant selected from the group consisting of an inorganic salt, a water absorbent polymer, a sugar, and desicated organismic matter, and water to form an admixture;

(b) maintaining said admixture under gelation conditions and for a period of time sufficient for said admixture to form an adherent granule; and (c) recovering said granule containing a pesticidally effective amount of said pest control agent.

2. The process according to claim 1 wherein said admixing comprises mixing an effective incorporating amount of a pregelatinized starch, a pesticidally effective amount of said pest control agent and an effective dispersant amount of a water dispersant with water to form an admixture, wherein said pest control agent is encapsulated in said pregelatinized starch.

3. The process according to claim 1 wherein said pregelatinized starch is fully pregelatinized pearl cornstarch, pearl cornstarch, waxy cornstarch, corn flour, potato amylopectin or a mixture thereof.

4. The process according to claim 1 wherein said pest control agent is a living pathogen, a chemical pesticide, a pest attractant, a pest phagostimulant or a mixture thereof.

5. The process according to claim 4 wherein said living pathogen is a bacterium, a fungus, a virus, a protozoa or a nematode.

6. The process according to claim 5 wherein said bacterium is *B. thuringiensis.*

7. The process according to claim 1 wherein said inorganic salt is a halide, a sulfate, a phosphate, a carbonate or a mixture thereof.

8. The process according to claim 1 wherein said inorganic salt is $CaCl_2$, $(NH_4)_2SO_4$, $Na_2SO_4$, KI, $FeCl_3$ or a mixture thereof.

9. The process according to claim 1 wherein said adherent granule is characterized by the property of being adherent to a plant surface.

10. The process according to claim 9 wherein said plant surface is a plant foliar surface.

11. The process according to claim 1 wherein said adherent granule is characterized by the property of being adherent to an external surface of an animal.

12. The process according to claim 11 wherein said external surface of an animal is skin, fur or hair.

13. A starch-based granule made by the process of claim 1.

14. A process of decreasing the population of a pest of a living organism comprising delivering to an external surface of said living organism a starch-based granule that (a) incorporates a pest control agent and (b) adheres to said surface and wherein said starch-based granule is made in accordance with the process of claim 1.

* * * * *